United States Patent
Akella et al.

(10) Patent No.: US 12,287,623 B2
(45) Date of Patent: Apr. 29, 2025

(54) METHODS AND SYSTEMS FOR AUTOMATICALLY CREATING STATISTICALLY ACCURATE ERGONOMICS DATA

(71) Applicant: R4N63R Capital LLC, Wilmington, DE (US)

(72) Inventors: Prasad Narasimha Akella, Palo Alto, CA (US); Ananya Honnedevasthana Ashok, Bangalore (IN); Zakaria Ibrahim Assoul, Oakland, CA (US); Krishnendu Chaudhury, Saratoga, CA (US); Sameer Gupta, Palo Alto, CA (US); Ananth Uggirala, Mountain View, CA (US)

(*) Notice: Subject to any disclaimer, the term of this patent is extended or adjusted under 35 U.S.C. 154(b) by 920 days.

(21) Appl. No.: 16/181,168

(22) Filed: Nov. 5, 2018

(65) Prior Publication Data

US 2019/0138676 A1     May 9, 2019

Related U.S. Application Data

(60) Provisional application No. 62/581,541, filed on Nov. 3, 2017.

(51) Int. Cl.
G05B 19/418     (2006.01)
G06F 9/448     (2018.01)
(Continued)

(52) U.S. Cl.
CPC ... *G05B 19/4183* (2013.01); *G05B 19/41835* (2013.01); *G06F 9/4498* (2018.02);
(Continued)

(58) Field of Classification Search
CPC . G16H 10/60; G06F 2111/20; G06F 2111/10; G06F 9/4498; G06F 16/24568;
(Continued)

(56) References Cited

U.S. PATENT DOCUMENTS 6,963,827 B1   11/2005   Elyea et al.
7,401,728 B2   7/2008   Markham et al.
(Continued)

FOREIGN PATENT DOCUMENTS

AU   2021245258 A1   4/2022
CN   106094707 A   11/2016
(Continued)

OTHER PUBLICATIONS

Gamze Uslu, RAM_ Real Time Activity Monitoring with feature extractive training, Elsevier, 2015.*
(Continued)

*Primary Examiner* — Miranda M Huang
*Assistant Examiner* — Sidney Vincent Bostwick
(74) *Attorney, Agent, or Firm* — Dorsey & Whitney LLP

(57) ABSTRACT

The systems and methods provide an action recognition and analytics tool for use in manufacturing, health care services, shipping, retailing and other similar contexts. Machine learning action recognition can be utilized to determine cycles, processes, actions, sequences, objects and or the like in one or more sensor streams. The sensor streams can include, but are not limited to, one or more video sensor frames, thermal sensor frames, infrared sensor frames, and or three-dimensional depth frames. The analytics tool can provide for analyzing ergonomic data from the one or more sensor streams.

15 Claims, 19 Drawing Sheets

(51) Int. Cl.

| | |
|---|---|
| *G06F 9/48* | (2006.01) |
| *G06F 11/07* | (2006.01) |
| *G06F 11/34* | (2006.01) |
| *G06F 16/22* | (2019.01) |
| *G06F 16/23* | (2019.01) |
| *G06F 16/2455* | (2019.01) |
| *G06F 16/901* | (2019.01) |
| *G06F 16/9035* | (2019.01) |
| *G06F 16/904* | (2019.01) |
| *G06F 30/20* | (2020.01) |
| *G06F 30/23* | (2020.01) |
| *G06F 30/27* | (2020.01) |
| *G06N 3/008* | (2023.01) |
| *G06N 3/04* | (2023.01) |
| *G06N 3/044* | (2023.01) |
| *G06N 3/045* | (2023.01) |
| *G06N 3/08* | (2023.01) |
| *G06N 3/084* | (2023.01) |
| *G06N 7/01* | (2023.01) |
| *G06N 20/00* | (2019.01) |
| *G06Q 10/06* | (2023.01) |
| *G06Q 10/0631* | (2023.01) |
| *G06Q 10/0639* | (2023.01) |
| *G06T 19/00* | (2011.01) |
| *G06V 10/25* | (2022.01) |
| *G06V 10/44* | (2022.01) |
| *G06V 10/82* | (2022.01) |
| *G06V 20/52* | (2022.01) |
| *G06V 40/20* | (2022.01) |
| *G09B 19/00* | (2006.01) |
| *B25J 9/16* | (2006.01) |
| *G01M 99/00* | (2011.01) |
| *G05B 19/423* | (2006.01) |
| *G05B 23/02* | (2006.01) |
| *G06F 18/21* | (2023.01) |
| *G06F 111/10* | (2020.01) |
| *G06F 111/20* | (2020.01) |
| *G06N 3/006* | (2023.01) |
| *G06Q 10/083* | (2023.01) |
| *G06Q 50/26* | (2012.01) |
| *G16H 10/60* | (2018.01) |

(52) U.S. Cl.
CPC ........ *G06F 9/4881* (2013.01); *G06F 11/0721* (2013.01); *G06F 11/079* (2013.01); *G06F 11/3452* (2013.01); *G06F 16/2228* (2019.01); *G06F 16/2365* (2019.01); *G06F 16/24568* (2019.01); *G06F 16/9024* (2019.01); *G06F 16/9035* (2019.01); *G06F 16/904* (2019.01); *G06F 30/20* (2020.01); *G06F 30/23* (2020.01); *G06F 30/27* (2020.01); *G06N 3/008* (2013.01); *G06N 3/04* (2013.01); *G06N 3/044* (2023.01); *G06N 3/045* (2023.01); *G06N 3/08* (2013.01); *G06N 3/084* (2013.01); *G06N 7/01* (2023.01); *G06N 20/00* (2019.01); *G06Q 10/06* (2013.01); *G06Q 10/063112* (2013.01); *G06Q 10/06316* (2013.01); *G06Q 10/06393* (2013.01); *G06Q 10/06395* (2013.01); *G06Q 10/06398* (2013.01); *G06T 19/006* (2013.01); *G06V 10/25* (2022.01); *G06V 10/454* (2022.01); *G06V 10/82* (2022.01); *G06V 20/52* (2022.01); *G06V 40/20* (2022.01); *G09B 19/00* (2013.01); *B25J 9/1664* (2013.01); *B25J 9/1697* (2013.01); *G01M 99/005* (2013.01); *G05B 19/41865* (2013.01); *G05B 19/423* (2013.01); *G05B 23/0224* (2013.01); *G05B 2219/32056* (2013.01); *G05B 2219/36442* (2013.01); *G06F 18/217* (2023.01); *G06F 2111/10* (2020.01); *G06F 2111/20* (2020.01); *G06N 3/006* (2013.01); *G06Q 10/083* (2013.01); *G06Q 50/26* (2013.01); *G16H 10/60* (2018.01)

(58) Field of Classification Search
CPC ............... G06F 16/904; G06F 16/9035; G06F 16/2228; G06F 16/2365; G06F 16/9024; G06F 30/20; G06F 9/4881; G06F 11/0721; G06F 11/079; B25J 9/1664; B25J 9/1697; G01M 99/005; G05B 19/41865; G05B 19/423; G05B 2219/32056; G05B 2219/36442; G05B 19/4183; G06K 9/6262; G06K 9/00335; G06N 3/006; G06N 20/00; G06N 3/008; G06N 3/04; G06N 3/0445; G06N 3/0454; G06N 3/08; G06N 3/084; G06N 7/005; G06Q 10/083; G06Q 50/26; G06Q 10/06; G06Q 10/063112; G06Q 10/06316
See application file for complete search history.

(56) References Cited

U.S. PATENT DOCUMENTS

| | | |
|---|---|---|
| 8,260,783 B2 | 9/2012 | Milam |
| 8,306,931 B1 | 11/2012 | Bowman et al. |
| 9,305,216 B1 | 4/2016 | Mishra |
| 9,471,610 B1 | 10/2016 | Long et al. |
| 9,921,726 B1 | 3/2018 | Sculley et al. |
| 10,445,702 B1 | 10/2019 | Hunt |
| 10,713,794 B1 | 7/2020 | He et al. |
| 10,852,712 B2 | 12/2020 | Ben-Bassat et al. |
| 11,226,720 B1 | 1/2022 | Vandivere et al. |
| 11,381,583 B1 | 7/2022 | Ellis et al. |
| 12,130,610 B2 | 10/2024 | Akella et al. |
| 2003/0229471 A1 | 12/2003 | Guralnik et al. |
| 2005/0105765 A1 | 5/2005 | Han et al. |
| 2005/0197803 A1 | 9/2005 | Eryurek et al. |
| 2006/0224254 A1 | 10/2006 | Rumi et al. |
| 2006/0241792 A1 | 10/2006 | Pretlove et al. |
| 2006/0271526 A1 | 11/2006 | Charnock et al. |
| 2009/0016599 A1 | 1/2009 | Eaton et al. |
| 2009/0016600 A1 | 1/2009 | Eaton et al. |
| 2009/0089227 A1 | 4/2009 | Sturrock et al. |
| 2010/0082512 A1 | 4/2010 | Myerson et al. |
| 2011/0043626 A1 | 2/2011 | Cobb et al. |
| 2012/0197898 A1 | 8/2012 | Pandey et al. |
| 2012/0198277 A1 | 8/2012 | Busser et al. |
| 2012/0225413 A1 | 9/2012 | Kotranza et al. |
| 2013/0234854 A1 | 9/2013 | Mukherjee et al. |
| 2013/0307693 A1 | 11/2013 | Stone et al. |
| 2013/0339923 A1 | 12/2013 | Xu et al. |
| 2014/0003710 A1 | 1/2014 | Seow et al. |
| 2014/0079297 A1 | 3/2014 | Tadayon et al. |
| 2014/0172357 A1 | 6/2014 | Heinonen |
| 2014/0222813 A1 | 8/2014 | Yang et al. |
| 2014/0275888 A1 | 9/2014 | Wegerich et al. |
| 2014/0277593 A1 | 9/2014 | Nixon et al. |
| 2014/0279776 A1 | 9/2014 | Brown et al. |
| 2014/0326084 A1 | 11/2014 | Bhushan |
| 2014/0337000 A1 | 11/2014 | Asenjo et al. |
| 2014/0379156 A1 | 12/2014 | Kamel et al. |
| 2015/0110388 A1 | 4/2015 | Eaton et al. |
| 2015/0282766 A1* | 10/2015 | Cole ............... A61B 5/1038 702/139 |
| 2015/0363438 A1 | 12/2015 | Botelho |
| 2015/0363741 A1 | 12/2015 | Chandra et al. |
| 2015/0364158 A1 | 12/2015 | Gupte et al. |
| 2016/0081594 A1* | 3/2016 | Gaddipati ......... A61B 5/1117 600/595 |
| 2016/0085607 A1 | 3/2016 | Marr et al. |

(56) References Cited

U.S. PATENT DOCUMENTS

| | | | |
|---|---|---|---|
| 2016/0148132 A1* | 5/2016 | Aqlan | G06Q 10/0635 705/7.16 |
| 2016/0322078 A1 | 11/2016 | Bose et al. | |
| 2016/0375524 A1 | 12/2016 | Hsu | |
| 2017/0046652 A1* | 2/2017 | Haldenby | G06Q 10/0631 |
| 2017/0098161 A1 | 4/2017 | Ellenbogen et al. | |
| 2017/0232613 A1 | 8/2017 | Ponulak et al. | |
| 2017/0243154 A1 | 8/2017 | Fletter et al. | |
| 2017/0245806 A1 | 8/2017 | Elhawary et al. | |
| 2017/0262697 A1 | 9/2017 | Kaps et al. | |
| 2017/0308800 A1 | 10/2017 | Cichon et al. | |
| 2017/0320102 A1 | 11/2017 | Mcvaugh et al. | |
| 2018/0011973 A1 | 1/2018 | Fish et al. | |
| 2018/0039745 A1 | 2/2018 | Chevalier et al. | |
| 2018/0056520 A1 | 3/2018 | Ozaki et al. | |
| 2018/0059630 A1 | 3/2018 | Yang et al. | |
| 2018/0096243 A1 | 4/2018 | Patil et al. | |
| 2018/0129888 A1 | 5/2018 | Schubert et al. | |
| 2018/0139309 A1 | 5/2018 | Pasam et al. | |
| 2018/0324199 A1 | 11/2018 | Crotinger et al. | |
| 2018/0330250 A1 | 11/2018 | Nakayama et al. | |
| 2018/0330287 A1 | 11/2018 | Tripathi | |
| 2019/0034734 A1 | 1/2019 | Yen et al. | |
| 2019/0058719 A1 | 2/2019 | Kar et al. | |
| 2019/0081876 A1 | 3/2019 | Ghare et al. | |
| 2019/0138971 A1 | 5/2019 | Uggirala et al. | |
| 2019/0266514 A1 | 8/2019 | Akella et al. | |
| 2019/0320898 A1 | 10/2019 | Dirghangi et al. | |
| 2020/0051203 A1 | 2/2020 | Nurvitadhi et al. | |
| 2020/0128307 A1 | 4/2020 | Li | |
| 2020/0188732 A1* | 6/2020 | Kruger | G06F 1/163 |
| 2020/0293972 A1 | 9/2020 | Arao et al. | |
| 2023/0343144 A1 | 10/2023 | Doy et al. | |

FOREIGN PATENT DOCUMENTS

| | | |
|---|---|---|
| CN | 107066979 A | 8/2017 |
| CN | 117594860 A | 2/2024 |
| EP | 2626757 | 8/2013 |
| EP | 2626757 A1 | 8/2013 |
| EP | 2996006 A1 | 3/2016 |
| WO | 2012141601 A2 | 10/2012 |
| WO | WO2012141601 | 10/2012 |
| WO | WO2017040167 | 3/2017 |
| WO | 2017091883 A1 | 6/2017 |
| WO | 2018009405 A1 | 1/2018 |

OTHER PUBLICATIONS

Yan, Xuzhong, et al. "Development of ergonomic posture recognition technique based on 2D ordinary camera for construction hazard prevention through view-invariant features in 2D skeleton motion." Advanced Engineering Informatics 34 (2017): 152-163. (Year: 2017).*

Wang, Keze, et al. "3d human activity recognition with reconfigurable convolutional neural networks." Proceedings of the 22nd ACM international conference on Multimedia. 2014. (Year: 2014).*

Weber, Michael, Christoph Rist, and J. Marius Zöllner. "Learning temporal features with CNNs for monocular visual ego motion estimation." 2017 IEEE 20th International Conference on Intelligent Transportation Systems (ITSC). IEEE, 2017. (Year: 2017).*

Zhang, Luming, et al. "Probabilistic graphlet transfer for photo cropping." IEEE Transactions on Image Processing 22.2 (2012): 802-815. (Year: 2012).*

Grinciunaite, Agne, et al. "Human pose estimation in space and time using 3d cnn." European Conference on Computer Vision. Cham: Springer International Publishing, 2016. (Year: 2016).*

Ji, Shuiwang, et al. "3D convolutional neural networks for human action recognition." IEEE transactions on pattern analysis and machine intelligence 35.1 (2012): 221-231. (Year: 2012).*

Xie, Saining, et al. "Rethinking spatiotemporal feature learning for video understanding." arXiv preprint arXiv:1712.04851 1.2 (2017): 5. (Year: 2017).*

Damiao, Alexandre, "convolution of images", retrieved from https://www.youtube.com/watch?v=YgtModJ-4cw, 2018 (Year: 2018).*

McMahon, Sean, et al. "Multimodal trip hazard affordance detection on construction sites." IEEE Robotics and Automation Letters 3.1 (2017): 1-8. (Year: 2017).*

Sepp Hochreiter & Jurgen Schmidhuber, *Long Short-Term memory*, Neural Computation, vol. 9, Issue 8, p. 1735-1780, Nov. 15, 1997.

Matthew Zeiler & Rob Fergus, Visualizing and Understanding Convolution Networks, arXiv;1311.2901v3, Nov. 28, 2013, pp. 11.

Ross Girshick, *Fast R-CNN*, Proceedings of the 2015 IEEE International Conference on Computer Vision (ICCV), p. 1440-1448, Dec. 7-13, 2015.

Shaoqing Ren et al., *Faster R-CNN: Towards Real Time Object Detection with Region Proposal Networks*, Proceedings of the 28th International Conference on Neural Information Processing Systems, vol. 1. p. 91-99, Dec. 7-12, 2015.

Christian Szegedy et al., *Inception-v4, Inception-Resnet and the Impact of Residual Connections on Learning*, ICLR 2016 Workshop, Feb. 18, 2016.

Jonathan Huang et al., *Speed/Accuracy Trade-Offs for Modern Convolutional Object Detectors*, Proceedings of the 2017 IEEE Conference on Computer Vision and Pattern Recognition (CVPR), Nov. 9, 2017.

Chen, L. , et al., "Sensor-Based Activity Recognition", in IEEE Transactions on Systems, Man, and Cybernetics, Part C (Applications and Reviews), vol. 42, No. 6, doi: 10.1109/TSMCC.2012. 2198883, Nov. 2012, pp. 790-808.

Girshick, Ross , "Fast R-CNN", Proceedings of the 2015 IEEE International Conference on Computer Vision (ICCV), Dec. 7-13, 2015, p. 1440-1448.

Huang, Jonathan , et al., "Speed/Accuracy Trade-Offs for Modern Convolutional Object Detectors", Proceedings of the 2017 IEEE Conference on Computer Vision and Pattern Recognition (CVPR), Nov. 9, 2017.

Ko, T. , "A Survey on Behavior Analysis in Video Surveillance for Homeland Security Applications", 2008 37th IEEE Applied Imagery Pattern Recognition Workshop, Washington, DC, USA, doi: 10.1109/AIPR.2008/4906450, 2008, pp. 1-8.

Sepp, Hochreiter , et al., "Long Short-Term Memory", Neural Computation, vol. 9, Issue 8, Nov. 15, 1997, p. 1735-1780.

Shaoqing, Ren , et al., "Faster R-CNN: Towards Real Time Object Detection with Region Proposal Networks", Proceedings of the 28th International Conference on Neural Information Processing Systems, vol. 1, Dec. 7-12, 2015, p. 91-99.

Szegedy, Christian , et al., "Inception-v4, Inception Resnet and the Impact of Residual Connections on Learning", ICLR 2016 Workshop, Feb. 18, 2016.

Zeiler, Matthew , et al., "Visualizing and Understanding Convolution Networks", arXiv; 1311.2901v3, Nov. 28, 2013, pp. 11.

* cited by examiner

| DATE & TIME | ACTION IDENTIFIED | STARTING COORDINATES | | | ENDING COORDINATES | | | WEIGHT | MOVEMENT DISTANCE (cm) |
|---|---|---|---|---|---|---|---|---|---|
| | | x | y | z | x1 | y1 | z1 | | P(x, y, z) - P(x1, y1, z1) |
| 23 Oct 17 | | | | | | | | | |
| 7:03:03 AM | Grab screwdriver | 32 | -2 | 12 | 22 | 21 | 21 | 2 lbs | 26.65 |
| 7:03:06 AM | Grab screws | -22 | -21 | 21 | -12 | -55 | 12 | | 43.12 |
| 7:03:08 AM | Unknown | 12 | 4 | 2 | 12 | 4 | 2 | | 38.85 |
| 7:03:12 AM | Affix 4 screws | 35 | -2 | 12 | 22 | 21 | 21 | 2 lbs | 5.44 |
| 7:03:16 AM | Grab chassis | -12 | -21 | 21 | -12 | -55 | 12 | 3 lbs | 34.23 |
| 7:03:22 AM | Unknown | 22 | 4 | 2 | 12 | 4 | 2 | | 26.65 |
| 7:03:28 AM | Position fans | 32 | -2 | 12 | 22 | 21 | 21 | | 2.12 |
| 7:03:36 AM | Screw fan 1 | -2 | -21 | 21 | -12 | -55 | 12 | 2 lbs | 3.21 |
| 7:03:46 AM | Screw fan 2 | 86 | -4 | 2 | -12 | 4 | 2 | 2 lbs | 5.44 |
| 7:03:56 AM | Screw fan 3 | 32 | -2 | 12 | 22 | 21 | 21 | 2 lbs | 4.23 |
| 7:04:03 AM | Screw fan 4 | -22 | -21 | 21 | -12 | -55 | 12 | 2 lbs | 2.01 |
| 7:04:06 AM | Unknown | 12 | 4 | 2 | 12 | 4 | 2 | | 2.12 |
| 7:04:08 AM | Unknown | 35 | -2 | 12 | 22 | 21 | 21 | | 4.45 |
| 7:04:12 AM | Grab hard-drive | -12 | -21 | 21 | -12 | -55 | 12 | 0.5 lbs | 65.44 |
| 7:04:16 AM | Grab screwdriver | 22 | 4 | 2 | 12 | 4 | 2 | 2 lbs | 26.23 |
| 7:04:22 AM | Grab screws | 32 | -2 | 12 | 22 | 21 | 21 | | 43.01 |
| 7:04:28 AM | Unknown | -2 | -21 | 21 | -12 | -55 | 12 | | 2.12 |
| 7:04:36 AM | Position hard drive | 86 | -4 | 2 | -12 | 4 | 2 | 1 lb | 4.45 |
| 7:04:46 AM | Screw hard drive 1 | 22 | 4 | 2 | 12 | 4 | 2 | 2 lbs | 5.32 |
| 7:04:56 AM | Screw hard drive 2 | 32 | -2 | 12 | 22 | 21 | 21 | 2 lbs | 5.87 |

FIG. 16

METHODS AND SYSTEMS FOR AUTOMATICALLY CREATING STATISTICALLY ACCURATE ERGONOMICS DATA

CROSS-REFERENCE TO RELATED APPLICATIONS

This application claim the benefit of U.S. Provisional Patent Application No. 62/581,541 filed Nov. 3, 2017, which is incorporated herein in its entirety.

BACKGROUND OF THE INVENTION

Even in this modern era, 90% of activities in factories are performed by humans and 10% by machines. The significance of this fuel becomes clear when noting that most/many of the techniques for measuring human activities to drive process optimization are very labor intensive, and effectively unchanged in a century. These techniques generally have their roots in 100-year-old systems such as Henry Ford's mass production, Frederick Taylor's Scientific Management movement, and Frank and Lillian Gilbreth's motion studies and "Therbligs" (which provided a vocabulary for translating the processes observed in time-and-motion studies into standardized data).

Today, the most common process optimization methodologies in use at many manufacturing (and non-manufacturing) organizations, such as Toyota's Lean Manufacturing and Motorola's Six-Sigma, rely on these manual techniques to gather data on human activities. The data gathered using these techniques represent a small and incomplete dataset. Worse, they represent a fundamentally biased dataset, since the person being measured may be "performing" for the observer and not providing truly representative samples of their work.

Thus, what is needed is a method for gathering data using modern and innovative techniques to implement a much more robust and complete dataset. What is further needed is an accurate dataset, that is not dependent upon whether people are conscious of being observed while performing their work. Since actors (including but not limited to humans and machines) have reach and payload limitations momentarily and cumulatively over time, what is further needed is a method and a system for continuously and automatically creating statistically accurate ergonomics data, personalized by the actor and the process, in order to better protect the actors. Safety insights from this data can be presented in real time or post-facto.

SUMMARY OF THE INVENTION

The present technology may best be understood by referring to the following description and accompanying drawings that are used to illustrate embodiments of the present technology directed toward real-time anomaly detection.

Embodiments of the present invention implement a method and system for automatically creating statistically accurate ergonomics data. Embodiments of the present invention implement a method for gathering data using modern and innovative techniques to implement a much more robust and complete dataset. Embodiments of the present invention implement an accurate dataset, that is not dependent upon whether people are conscious of being observed while performing their work. Embodiments of the present invention implement a method and a system for automatically creating statistically accurate ergonomics data. Embodiments of this present invention enable personalization of data for the actor and the process. Embodiments of the present invention enable better protection of the actors (including but not limited to humans and machines) since actors may exceed reach and payload limitations momentarily or cumulatively over time. Embodiments of this invention enable the presentation of these safety insights in real time or post-facto.

Embodiments of the present invention implement a technology that non-intrusively digitizes actions performed by both humans and machines using deep neural networks (refer to provisional patent: "Deep Learning System for Real-Time Analysis of Manufacturing Operations" for high-level description). By digitizing actions performed, embodiments of the present invention convert them into data that can be applied for process optimization. Embodiments of the present invention use technology that enables human activities to be measured automatically, continuously and at scale.

While one initial focus is in manufacturing, the technology is applicable to human activity in any setting. Embodiments of the present invention enable the creation of a fundamentally new dataset of human actions. This dataset includes quantitative data (which actions were performed by which person, at which station, on which specific part, at what time), judgments based on performance data (person X performs bettor/worse than average), and inferences based on an understanding of the process (product Y exited the line with incomplete tasks). This dataset enables embodiments of the present invention to fundamentally re-imagine many of the techniques used to optimize manual and automated processes from manufacturing to the service industry.

Beyond the measurement of actions, embodiments of the present invention implement a system that is capable of performing the aforementioned process validation in real time or in seconds, and that is, identifying which activity is being performed, determining whether or not the action conforms to the correct process, and communicating information about process adherence/deviation back to the actor performing the action or to other interested parties. This further expands the range of business applications to which embodiments of the present invention can be applied, either new or re-imagined.

Embodiments of the present invention enable a number of applications by instrumenting a workstation, recording data (e.g., video, audio, thermal, vibration) from this workstation, labeling the actions in this data, building deep learning models, training these models to find the best predictor, and then inferring the actions observed in the data feed(s), possibly in real-time driving business processes with this data.

Embodiments of the present invention can identify spatiotemporal information of the worker performing his or her required tasks. In one embodiment, since the camera is not always placed orthogonal to the worker, the data it captures can be distorted, based on the camera's viewpoint. Using camera coordinates and image projection techniques, the worker's hand coordinates (x, y, z) can be established accurately. Embodiments of the present invention can then continuously collect spatial data of worker's body parts (e.g., hands) as she executes tasks on the assembly line. In more sophisticated analyses, (e.g., 3D, x, y, z, roll, pitch, yaw) data is collected along with a synchronized time stamp. With this data, embodiments of the present invention can determine and output, reach studies using statistical analysis over time (distance), motion studies using statistical analyst over time (distance and frequency), repetitive motion analysis studies (distance, frequency and count), torque and load studies (force, frequency and count), and reports identifying unsafe conditions that are created by integrating the present technology's spatial with OSHA ergonomic rules (reach, repetition frequency, etc.). In one embodiment, these reports can be delivered on a scheduled or an ad hoc basis when certain pre-specified conditions established by regulatory requirements or scientific work are identified.

As stated earlier, current techniques require manual generation of time and motion data, a process that is fundamentally limiting and flawed. In contrast, by generating large volumes of data and non-dimensionalizing the data in new and creative ways, embodiments of the present invention enable analysis of repetitive motion injury. This enables embodiments of the present invention to, based on a large data set, uniquely, provide insights into the inherent safety of the work environment for workers and address a top priority for most manufacturers.

Embodiments of the present invention collect time and motion data as described above. In reach studies, embodiments of the present invention, a point cloud map, a heat map or the like, of the places in the work space that the worker reaches out to can be constructed from the spatio-temporal data captured by the system. Additionally, similar representations of two-dimensional projections of the three-dimensional data can be constructed. Further, embodiments of the present invention can produce continuous motion data from worker's hands starting position (e.g., x, y, z) to ending position (e.g., x1, y1, z1). This data can be analyzed over a time-period for repetitive motions to identity longer term ergonomic issues.

In this manner, embodiments of the present invention are directed to providing an ergonomic correct environment. In one embodiment, activity of a human actor is monitored and analyzed. The analysis can have a predictive element/nature (e.g. predict movement/result to determine if a dangerous condition/collision is going to happen before bad event happens). Feedback on a corrective action can be provided to the actors (e.g., an alarm of collision/dangerous condition, an order for robot to stop/take evasive measure, etc.). Compliance of the actor with safety guidelines can be checked and alarm forwarded if not.

In one embodiment, the present invention is implemented as a method that includes accessing information associated with a first actor, including sensed activity information associated with an activity space, analyzing the activity information, including analyzing activity of the first actor with respect to ergonomic factors, and forwarding feedback on the results of the analysis, wherein the results includes identification of economically problematic activities.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which:

FIG. 16 shows an exemplary ergonomics data table, in accordance with aspects of the present technology.

DETAILED DESCRIPTION OF THE INVENTION

Figure 1:
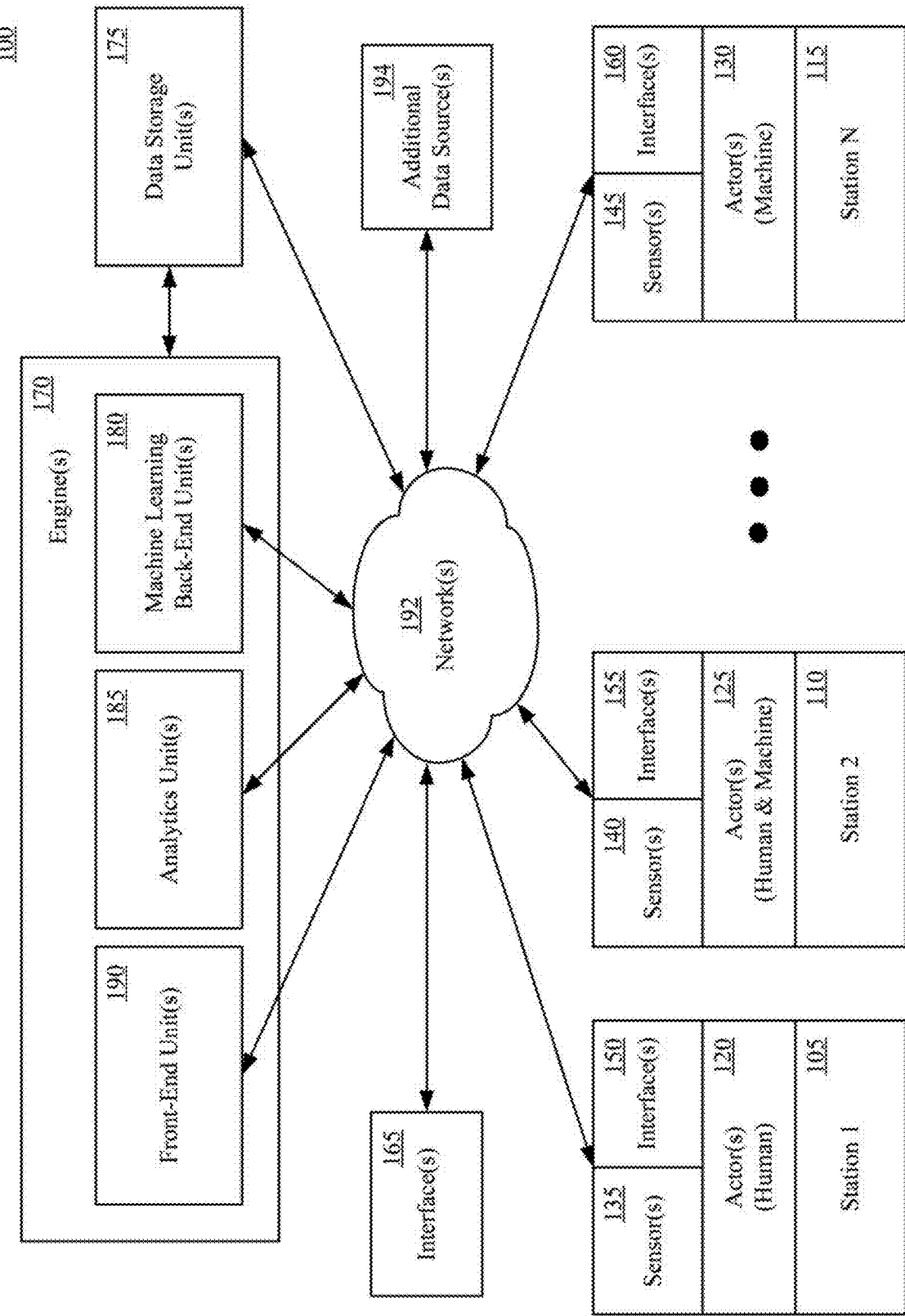
FIG. 1 shows an action recognition and analytics system, in accordance with aspect of the present technology.

Reference will now be made in detail to the embodiments of the present technology, examples of which are illustrated in the accompanying drawings. While the present technology will be described in conjunction with these embodiments, it will be understood that they are not intended to limit the invention to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations lake the form of electric or magnetic signals capable of being stored, transferred, compared and otherwise manipulated m an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that all of these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

As used herein, the use of the disjunctive is intended to include the conjunctive. The use of definite or indefinite articles is not intended to indicate cardinality. In particular, a reference to "the" object or "a" object is intended to denote also one of a possible plurality of such objects. It is also to be understood that the phraseology and terminology used herein is for the purpose of description and should not be regarded as limiting.

As used herein the term process can include processes, procedures, transactions, routines, practices, and the like. As used herein the term sequence can include sequences, orders, arrangements, and the like. As used herein the term action can include actions, steps, tasks, activity, motion, movement and the like. As used, herein the term object can include objects, parts, components, items, elements, pieces, assemblies, sub-assemblies, and the like. As used herein a process can include a set of actions or one or more subsets of actions, arranged in one or more sequences, and performed on one or more objects by one or more actors. As used herein a cycle can include a set of process or one or more subsets of processes performed in one or more sequences. As used herein a sensor stream can include a video sensor stream, thermal sensor stream, infrared sensor stream, hyperspectral sensor stream, audio sensor stream, depth data stream, and the like. As used herein frame based sensor stream can include any sensor stream that can be represented by a two or more dimensional array of data values. As used herein the term parameter can include parameters, attributes, or the like. As used herein the form indicator can include indicators, identifiers, labels, tags, states, attributes, values or the like. As used herein the term feedback can include feedback, commands, directions, alerts, alarms, instructions, orders, and the like. As used herein the term actor can include actors, workers, employees, operators, assemblers, contractors, associates, managers, users, entities, humans, cobots, robots, and the like as well as combinations of them. As used herein the term robot can include a machine, device, apparatus or the like, especially one programmable by a computer, capable of carrying out a series of actions automatically. The actions can be autonomous, semi-autonomous, assisted, or the like. As used herein the term cobot can include a robot intended to interact with humans in a shared workspace. As used herein the term package can include packages, packets, bundles, boxes, containers, cases, cartons, kits, and the like. As used herein, real time can include responses within a given latency, which can vary from sub-second to seconds.

Referring to FIG. 1 an action recognition and analytics system, in accordance with aspect of the present technology, is shown. The action recognition and analytics system 100 can be deployed in a manufacturing, health care, warehousing, shipping, retail, restaurant or similar context. A manufacturing context, for example, can include one or more stations 105-115 and one or more actors 120-130 disposed at the one or more stations. The actors can include humans, machine or any combination therefore. For example, individual or multiple workers can be deployed at one or more stations along a manufacturing assembly line. One or more robots can be deployed at other stations. A combination of one or more workers and/or one or more robots can be deployed additional stations It is to be noted that the one or more stations 105-115 and the one or more actors are not generally considered to be included in the system 100.

In a health care implementation, an operating room can comprise a single station implementation. A plurality of sensors, such as video cameras, thermal imaging sensors, depth sensors, or the like, can be disposed non-intrusively at various positions around the operating room. One or more additional sensors, such as audio, temperature, acceleration, torque, compression, tension, or the like sensors, can also be disposed non-intrusively at various positions around the operating room.

In a shipping implementation, the plurality of stations may represent different loading docks, conveyor belts, forklifts, sorting stations, holding areas, and the like. A plurality of sensors, such as video cameras, thermal imaging sensors, depth sensors, or the like, can be disposed non-intrusively at various positions around the loading docks, conveyor belts, forklifts, sorting stations, holding areas, and the like. One or more additional sensors, such as audio, temperature, acceleration, torque, compression, tension, or the like sensors, can also be disposed non-intrusively at various positions.

In a retailing implementation, the plurality of stations may represent one or more loading docks, one or more stock rooms, the store shelves, the point of sale (e.g. cashier stands, self-checkout stands and auto-payment geofence), and the like. A plurality of sensors such as video cameras, thermal imaging sensors, depth sensors, or the like, can be disposed non-intrusively at various positions around the loading docks, stock rooms, store shelves, point of sale stands and the like. One or more additional sensors, such as audio, acceleration, torque, compression, tension, or the like sensors, can also be disposed non-intrusively at various positions around the loading docks, stock rooms, store shelves, point of sale stands and the like.

In a warehousing or online retailing implementation, the plurality of stations may represent receiving areas, inventory storage, picking totes, conveyors, packing areas, shipping areas, and the like. A plurality of sensors, such as video cameras, thermal imaging sensors, depth sensors, or the like, can be disposed non-intrusively at various positions around the receiving areas, inventory storage, picking totes, conveyors, packing areas, and shipping areas. One or more additional sensors, such as audio, temperature, acceleration, torque, compression, tension, or the like sensors, can also be disposed non-intrusively at various positions.

Aspect of the present technology will be herein further described with reference to a manufacturing context so as to best explain the principles of the present technology without obscuring aspects of the present technology. However, the present technology as further described below can also be readily applied in health care, warehousing, shipping, retail, restaurants, and numerous other similar contexts.

The action recognition and analytics system 100 can include one or more interfaces 135-165. The one or more interface 135-145 can include one or more sensors 135-145 disposed at the one or more stations 105-115 and configured to capture streams of data concerning cycles, processes, actions, sequences, object, parameters and or the like by the one or more actors 120-130 and or at the station 105-115. The one or more sensors 135-145 can be disposed non-intrusively, so that minimal to changes to the layout of the assembly line or the plant are required, at various positions around one or more of the stations 105-115. The same set of one or more sensors 135-145 can be disposed at each station 105-115, or different sets of one or more sensors 135-145 can be disposed at different stations 105-115. The sensors 135-145 can include one or more sensors such as video cameras, thermal imaging sensors, depth sensors, or the like. The one or more sensors 135-145 can also include one or more other sensors, such as audio, temperature, acceleration, torque, compression, tension, or the like sensors.

The one or more interfaces 135-165 can also include but not limited to one or more displays, touch screens, touch pads, keyboards, pointing devices, button, switches, control panels, actuators, indicator lights, speakers, Augmented Reality (AR) interfaces, Virtual Reality (VR) interfaces, desktop Personal Computers (PCs), laptop PCs, tablet PCs, smart phones, robot interfaces, cobot interfaces. The one or more interfaces 135-165 can be configured to receive inputs from one or more actors 120-130, one or more engines 170 or other entitles. Similarly, the one or more interfaces 135-165 can be configured to output to one or more actors 120-130, one or more engine 170 or other entities. For example, the one or more front-end units 190 can output one or more graphical user interfaces to present training content, work charts, real time alerts, feedback and or the like on one or more interfaces 165, such displays at one or more stations 120-130, at management portals on tablet PCs, administrator portals as desktop PCs or the like. In another example, the one or more front-end units 190 can control an actuator to push a defective unit of the assembly line when a defect is detected. The one or more front-end units can also receive responses on a touch screen display device, keyboard, one or more buttons, microphone or the like from one or more actors. Accordingly, the interfaces 135-165 can implement an analysis interface, mentoring interface and or the like of the one or more front-end units 190.

The action recognition and analytics system 100 can also include one or more engines 170 and one or more data storage units 175. The one or more interfaces 135-165, the one or more data storage units 175, the one or more machine learning back-end units 180, the one or more analytics units 185, and the one or more front-end units 190 can be coupled together by one or more networks 192. It is also to be noted that although the above described elements are described as separate elements, one or more elements of the action recognition and analytics system 100 can be combined together or further broken into different elements.

The one or more engines 170 can include one or more machine learning back-end units 180, one or more analytics units 185, and one or more front-end units 190. The one or more data storage units 175, the one or more machine learning back-end units 180, the one or more analytics units 185, and the one or more analytics front-end units 190 can be implemented on a single computing device, a common set of computing devices, separate computing device, or different sets of computing devices that can be distributed across the globe inside and outside an enterprise. Aspects of the one or more machine learning back-end units 180, the one or more analytics units 185 and the one or more front-end units 190, and or other computing units of the action recognition and analytics system 100 can be implemented by one or more central processing units (CPU), one or more graphics processing units (GPU), one or more tensor processing units (TPU), one or more digital signal processors (DSP), one or more microcontrollers, one or more field programmable gate arrays and or the like, and any combination thereof. In addition, the one or more data storage units 175, the one or more machine learning back-end units 180, the one or more analytics units 185, and the one or more front-end units 190 can be implemented locally to the one or more stations 105-115, remotely from the one or more stations 105-115, or any combination of locally and remotely. In one example, the one or more data storage units 175, the one or more machine learning back-end units 180, the one or more analytics unite-185, and the one or more front-end units 190 can be implemented on a server local (e.g., on site at the mams tourer) to the one or more stations 105-115. In another example, the one or more machine learning back-end units 135, the one or more storage units 140 and analytics front-end units 145 can be implemented on a cloud computing service remote from the one or more stations 105-115. In yet another example, the one or more data storage units 175 and the one or more machine learning back-end units 180 can be implemented remotely on a server of a vendor, and one or more data storage units 175 and the one or more front-end units 190 are implemented locally on a server or computer of the manufacturer. In other examples, the one or more sensors 135-145, the one or more machine learning back-end units 180, the one or more front-end unit 190, and other computing units of the action recognition and analytics system 100 can perform processing at the edge of the network 192 in an edge computing implementation. The above example of the deployment of one or more computing devices to implement the one or more interfaces 135-165, the one or more engines 170, the one or more data storage units 140 and one or more analytics front-end units 145, are just some of the many different configuration for implementing the one or more machine learning back-end units 135, one or more data storage units 140. Any number of computing devices, deployed locally, remotely, at the edge or the like can be utilized for implementing the one or more machine learning back-end units 135, the one or more data storage units 140, the one or more analytics front-end units 145 or other computing units.

The action recognition and analytics system 100 can also optionally include one or more data compression units associated with one or more of the interfaces 135-165. The data compression units can be configured to compress or decompress data transmitted between the one or more interface 135-165, and the one or more engines 170. Data compression, for example, can advantageously allow the sensor data from the one or more interface 135-165 to be transmitted across one or more existing networks 192 of a manufacturer. The data compression units can also be integral to one or more interfaces 135-165 or implemented separately. For example, video capture sensors may include an integral Motion Picture Expert Group (MPEG) compression unit (e.g., H-264 encoder/decoder). In an exemplary implementation, the one or more data compression units can use differential coding and arithmetic encoding to obtain a 20× reduction in the size of depth data from depth sensors. The data from a video capture sensor can comprise roughly 30 GB of H.264 compressed data per camera, per day for a factory operation with three eight-hour shifts. The depth data can comprise roughly another 400 GB of uncompressed data per sensor, per day. The depth data can be compressed by an algorithm to approximately 20 GB per sensor, per day. Together, a set of a video sensor and a depth sensor can generate approximately 50 GB of compressed data per day. The compression can allow the action recognition and analytics system 100 to use a factory's network 192 to move and store data locally or remotely (e.g., cloud storage).

The action recognition and analytics system 100 can also be communicatively coupled to additional data sources 194, such as but not limited to a Manufacturing Execution Systems (MES), warehouse management system, or patient management system. The action recognition and analytics system 100 can receive additional data, including one or more additional sensor streams, from the additional data sources 194. The action recognition and analytics system 100 can also output data, sensor streams, analytics result and or the like to the additional data sources 194. For example, the action recognition can identify a barcode on an object and provide the barcode input to a MES for tracking.

The action recognition and analytics system 100 can continually measure aspects of the real-world, making it possible to describe a context utilizing vastly more detailed data sets, and to solve important business problems like line balancing, ergonomics, and or the like. The data can also reflect variations over time. The one or more machine learning back-end units 170 can be configured to recognize, in real time, one or more cycles, processes, actions, sequences, objects, parameters and the like in the sensor streams received from the plurality of sensors 135-145. The one or more machine learning back-end units 180 can recognize cycles, processes, actions, sequences, objects, parameters and the like in sensor streams utilizing deep learning, decision tree learning, inductive logic programming, clustering, reinforcement learning, Bayesian networks, and or the like.

Figure 2:
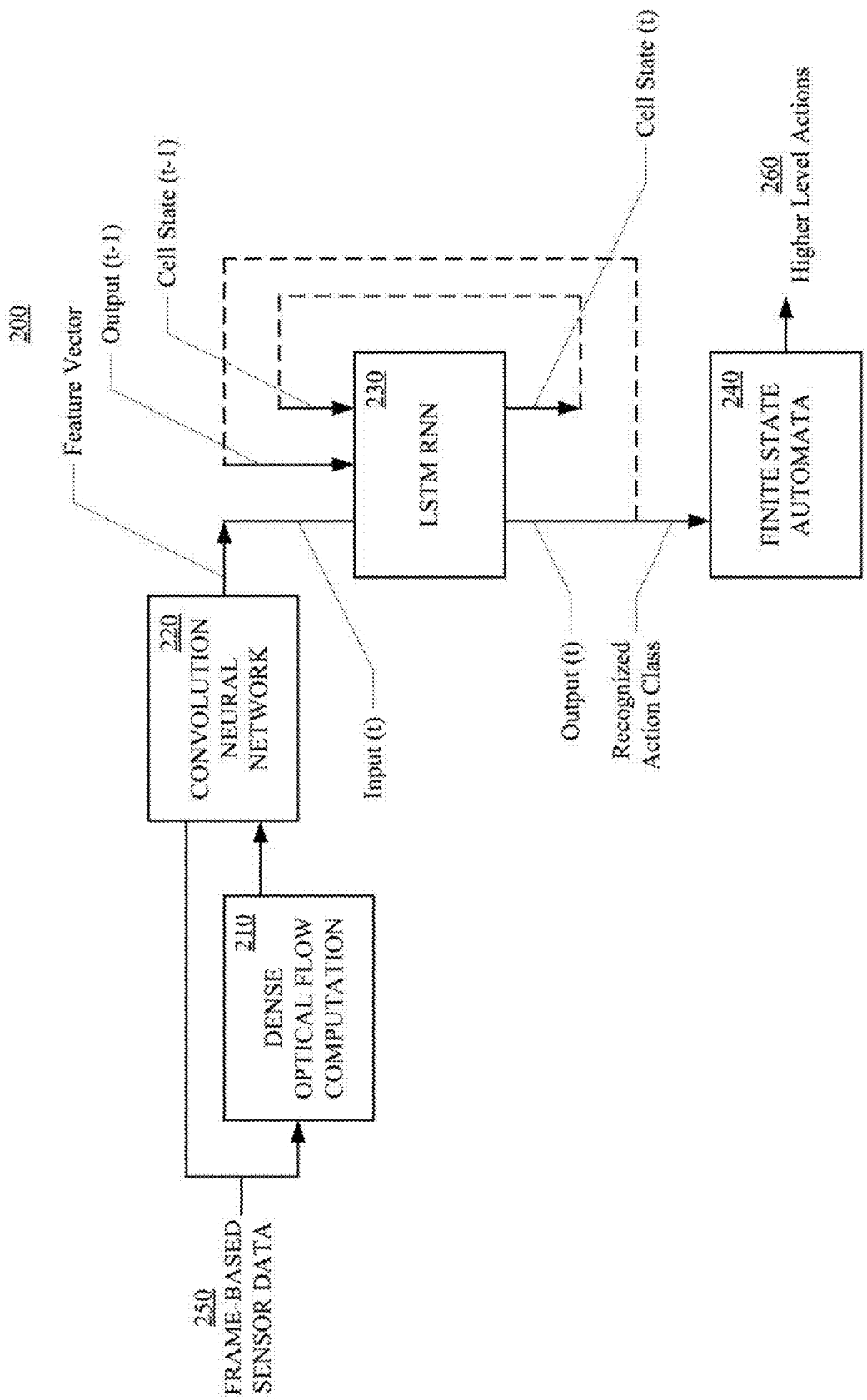
FIG. 2 shows an exemplary deep learning type machine learning back-end unit, in accordance with aspects of the present technology.

Referring now to FIG. 2, an exemplary deep learning type machine learning back-end unit, in accordance with aspects of the present technology, is shown. The deep learning unit 200 can be configured to recognize, in real time, one or more cycles, processes, actions, sequences, objects, parameters and the like in the sensor streams received from the plurality of sensors 120-130. The deep learning unit 200 can include a dense optical flow computation unit 210, a Convolution Neural Networks (CNNs) 220, a Long Short Term Memory (LSTM) Recurrent Neural Network (RNN) 230, and a Finite State Automata (FSA) 240. The CNNs 220 can be based on two-dimensional (2D) or three-dimensional (3D) convolutions. The dense optical flow computation unit 210 can be configured to receive a stream of frame-based sensor data 250 from sensors 120-130. The dense optical flow computation unit 210 can be configured to estimate an optical flow, which is a two-dimension (2D) vector held where each vector is a displacement vector showing the movement of points from a first frame to a second frame. The CNNs 220 can receive the stream of frame-based sensor data 250 and the optical flow estimated by the dense optical flow computation unit 210. The CNNs 220 can be applied to video frames to create a digest of the frames. The digest of the frames can also be referred to as the embedding vector. The digest retains those aspects of the frame that help in identifying actions, such as the core visual clues that are common to instances of the action in question.

In a three-dimensional Convolution Neural Network (3D CNN) based approach, spatio-temporal convolutions can be performed to digest multiple video femes together to recognize actions. For 3D CNN, the first two dimension can be along space, and in particular the width and height of each video frame. The third dimension can be along time. The neural network can learn to recognize actions not just from the spatial pattern in individual frame, but also jointly in space and time. The neural network is not just using color patterns in one frame to recognize actions. Instead, the neural network is using how the pattern shifts with time (i.e., motion cues) to come up with its classification. According the 3D CNN is attention driven, in that it proceeds by identifying 3D spatio-temporal bounding boxes as Regions of Interest (RoI) and focusses on them to classify actions.

In one implementation, the input to the deep teaming unit 200 can include multiple data streams. In one instance, a video sensor signal, which includes red, green and blue data streams, can comprise three channels. Depth image data can comprise another channel. Additional channels can accrue from temperature, sound, vibration, data from sensors (e.g., torque from a screwdriver) and the like. From the RGB and depth streams, dense optical flow fields can be computed by the dense optical flow computation unit 210 and fed to the Convolution Neural Networks (CNNs) 220. The RGB and depth streams can also be fed to the CNNs 220 as additional streams of derived data.

The Long Short Term Memory (LSTM) Recurrent Neural Network (RNN) 230 can be fed the digests from the output of the Convolution Neural Networks (CNNs) 270. The LSTM can essentially be a sequence identifier that is trained to recognize temporal sequences of sub-events that constitute an action. The combination of the CNNs and LSTM can be jointly trained, with full back-propagation, to recognize low-level actions. The low-level actions can be referred to as atomic actions, like picking a screw, picking a screwdriver, attaching screw to screwdriver and the like. The Finite State Automata (FSA) 240 can be mathematical models of computations that include a set of state and a set of rules that govern the transition between the states based on the provided input. The FSA 240 can be configured to recognize higher-level actions 260 from the atomic actions. The high-level actions 260 can be referred to as molecular actions, for example turning a screw to affix a hard drive to a computer chassis. The CNNs and LSTM can be configured to perform supervised training on the data from the multiple sensor streams. In one implementation, approximately 12 hours of data, collected over the course of several days, can be utilized to train the CNNs and LSTM combination.

Figure 3:
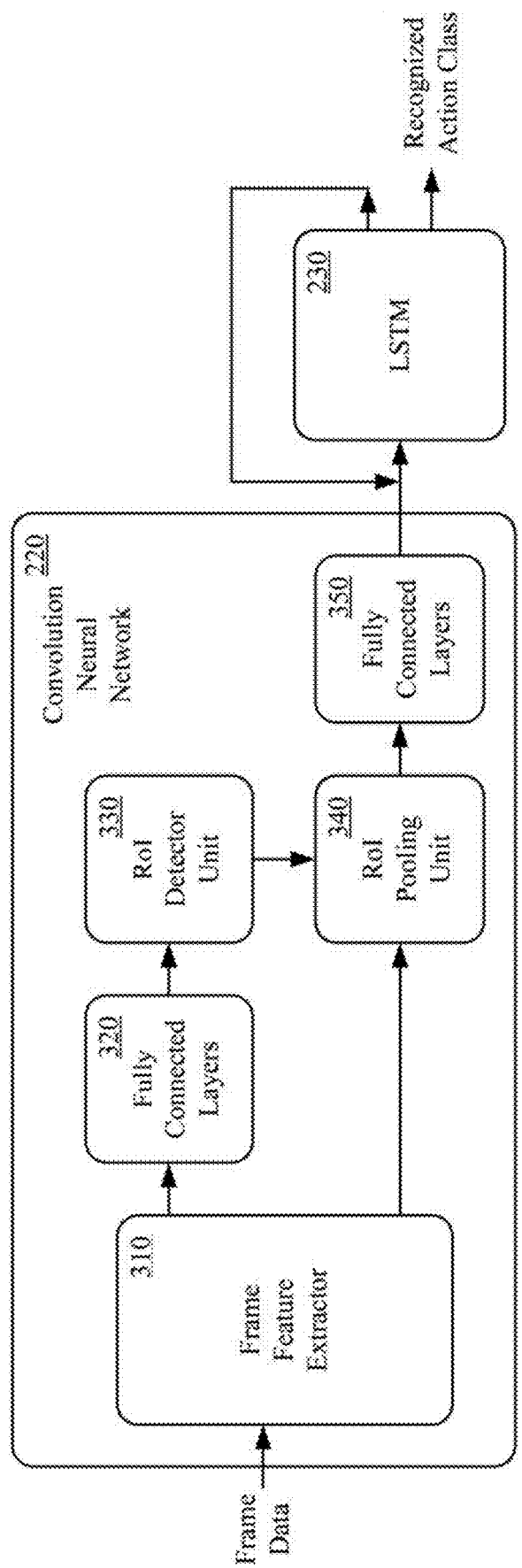
FIG. 3 shows an exemplary Convolution Neural Network (CNN) and Long Short Term Memory (LSTM) Recurrent Neural Network (RNN), in accordance with aspects of the present technology.
Figure 4:
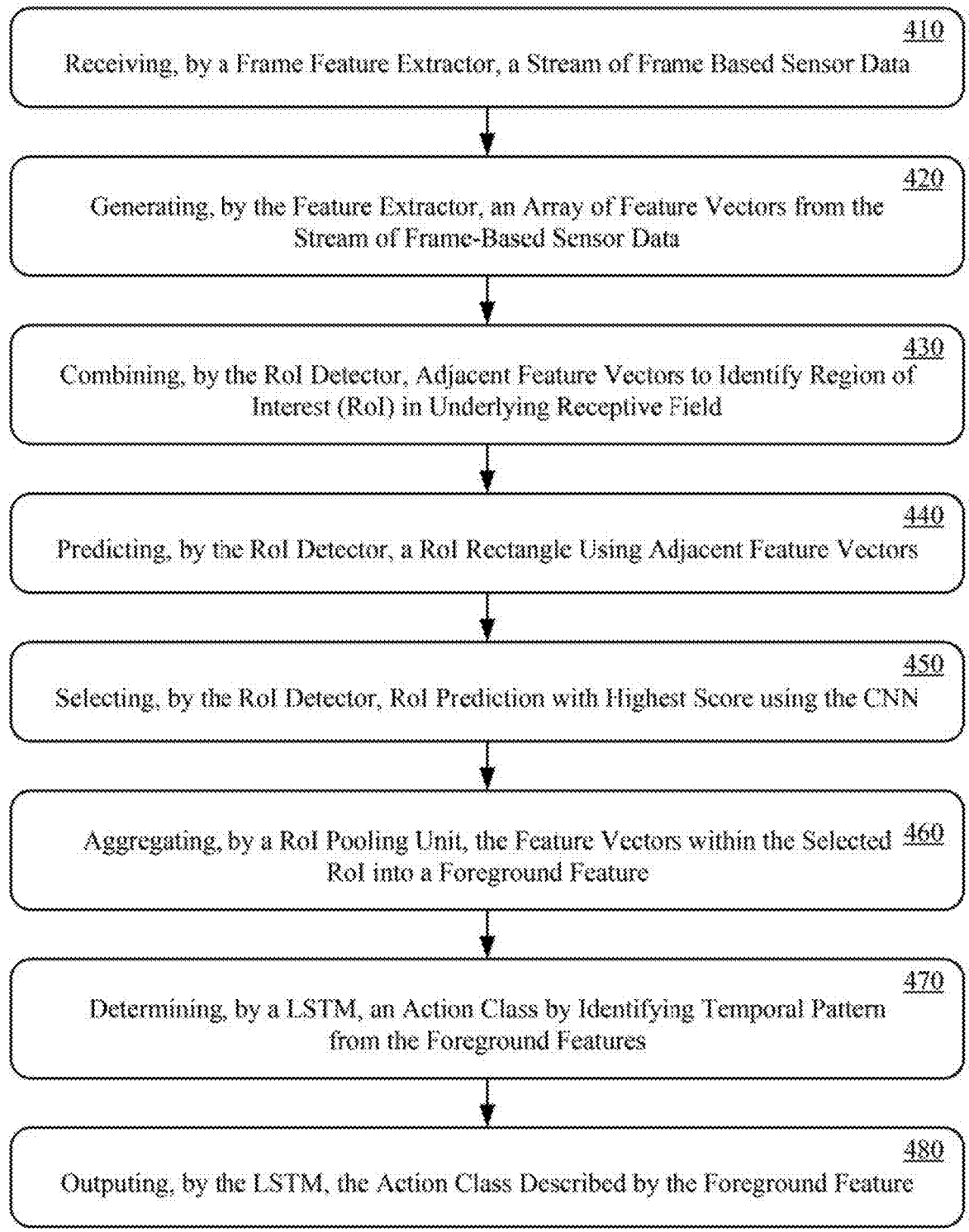
FIG. 4 shows an exemplary method of detecting actions in a sensor stream, in accordance with aspects of the present technology.

Referring now to FIG. 3, an exemplary Convolution Neural Networks (CNNs) and Long Short Term Memory (LSM) Recurrent Neural Network (RNN), in accordance with aspects of the present technology, is shown. The CNNs can include a frame feature extractor 310, a first Fully Connected (FC) layer 320, a Region of Interest (RoI) detector unit 330, a RoI pooling unit 340, and a second Fully Connected (FC) layer 350. The operation of the CNNs and LSTM will be further explained with reference to FIG. 4, which shows an exemplary method of detecting actions in a sensor stream.

The frame feature extractor 310 of the Convolution Neural Networks (CNNs) 220 can receive a stream of frame-based sensor data, at 410. At 420, the frame feature extractor 310 can perform a two-dimensional convolution operation on the received video frame and generate a two-dimensional array of feature vectors. The frame feature extractor 310 can work on the full resolution image, wherein a deep network is effectively sliding across the image generating a feature vector at each stride position. Thus, each element of the 2D feature vector array is a descriptor for the corresponding receptive field (e.g., fixed portion of the underlying image). The first Fully Connected (PC) layer can flatten the high-level features extracted by the frame feature extractor 310, and provide additional non-linearity and expressive power, enabling the machine to learn complex non-linear combinations of these features.

At 430, the RoI detector unit 330 can combine neighboring feature vectors to make a decision on whether the underlying receptive field belongs to a Region of Interest (RoI) or not. If the underlying receptive field belongs to a RoI, a RoI rectangle can be predicted from the same set of neighboring feature vectors, at 440. At, 450, a RoI rectangle with a highest score can be chosen by the RoI detector unit 330. For the chosen RoI rectangle, the feature vectors lying within it can be aggregated by the RoI pooling unit 340, at 460. The aggregated feature vector is a digest/descriptor for the foreground for that video frame.

In one implementation, the RoI detector unit 330 can determine a static RoI. The static RoI Identifies a Region of Interest (RoI) within an aggregate set of feature vectors describing a video frame, and generates a RoI area for the identified RoI. A RoI area within a video frame can be indicated with a RoI rectangle that encompasses an area of the video frame designated for action recognition, such as an area in which actions are performed in a process. Alternatively, the RoI area can be designated with a box, circle, highlighted screen, or any other geometric shape or indicator having various scales and aspect ratios used to encompass a RoI. The area within the RoI rectangle is the area within the video frame to be processed by the Long Short Term Memory (LSTM) for action recognition.

The Long Short Term Memory (LSTM) can be trained using a RoI rectangle that provides, both, adequate spatial context within the video frame to recognize actions and independence from irrelevant portions of the video frame in the background. The trade-off between spatial context and background independence ensures that the static RoI detector can provide clues tor the action recognition while avoiding spurious unreliable signals within a given video frame.

In another implementations, the RoI detector unit 330 can determine a dynamic RoI. A RoI rectangle can encompass areas within a video frame in which an action is occurring. By focusing on areas in which action occurs, the dynamic RoI detector enables recognition of actions outside of a static RoI rectangle while relying on a smaller spatial context, or local context, than that used to recognize actions in a static RoI rectangle.

In one implementation, the RoI pooling unit 340 extracts a fixed-sized feature vector from the area within an identified RoI rectangle, and discards the remaining feature vectors of the input video frame. The fixed-sized feature vector, or foreground feature, includes the feature vectors generated by the video frame feature extractor that are located within the coordinates indicating a RoI rectangle as determined by the RoI detector unit 330. Because the RoI pooling unit 340 discards feature vectors act included within the RoI rectangle, the Convolution Neural Networks (CNNs) 220 analyzes actions within the RoI only, thus ensuring that unexpected changes in the background of a video frame are not erroneously analyzed for action recognition.

In one implementation, the Convolution Neural Networks (CNNs) 220 can be an Inception ResNet. The Inception ResNet can utilize a sliding window style operation. Successive convolution layers output a feature vector at each point of a two-dimensional grid. The feature vector at location (x,y) at level l can be derived by weighted averaging features from a small local neighborhood (aka receptive field) N around the (x,y) at level l-1 followed by a pointwise non-linear operator. The non-linear operator can be the RELU (max(0,x)) operator.

In the sliding window, there can be many more than 7×7 points at the output of the last convolution layer. A Fully Connected (FC) convolution can be taken over the feature vectors from the 7×7 neighborhoods, which is nothing but applying one more convolution. The corresponding output represents the Convolution Neural Networks (CNNs) output at the matching 224×224 receptive field on the input image. This is fundamentally equivalent to applying the CNNs to each sliding window stop. However, no computation is repeated, thus keeping the inferencing computation cost real time on Graphics Processing Unit (GPU) based machines.

The convolution layers can be shared between RoI detector 330 and the video frame feature extractor 310. The RoI detector unit 330 can identify the class independent rectangular region of interest from the video frame. The video frame feature extractor can digest, the video frame into feature vectors. The sharing of the convolution layers improves efficiency, wherein these expensive layers can be run once per frame and the results saved and reused.

One of the outputs of the Convolution Neural Networks (CNNs) is the static rectangular Region of Interest (RoI). The term "static" as used herein denotes that the RoI does not vary greatly from frame to frame, except when a scene change occurs, and it is also independent of the output class.

A set of concentric anchor boxes can be employed at each sliding window stop. In one implementation, there can be nine anchor boxes per sliding window stop for combinations of 3 scales and 3 aspect ratios. Therefore, at each sliding window stop there are two set of outputs. The first set of outputs can be a Region of Interest (RoI) present/absent that includes 18 outputs of the form 0 or 1. An output of 0 indicates the absence of a RoI within the anchor box, and an output of 1 indicates the presence of a RoI within the anchor box. The second set of outputs can include Bounding Box (BBox) coordinates including 36 floating point outputs indicating the actual BBox for each of the 9 anchor boxes. The BBox coordinates are to be ignored if the RoI present/absent output indicates the absence of a RoI.

For training, sets of video frames with a per-frame Region of Interest (RoI) rectangle are presented to the network. In frames without a RoI rectangle, a dummy 0×0 rectangle can be presented. The Ground Truth for individual anchor boxes can be created via the Intersection over Union (IoU) of rectangles. For the $i_{th}$ anchor box $\vec{b}_i = \{x_i, y_i, w_i, h_i\}$ the derived Ground Truth for the RoI presence probability can be determined by Equation 1:

$$p_i^* = \begin{cases} 1 & IoU(\vec{b}_i, \vec{g}) >= 0.7 \\ 0 & IoU(\vec{b}_i, \vec{g}) <= 0.1 \\ \text{box unused for training} \end{cases}$$

where $\vec{g} = \{x_g, y_g, w_g, h_g\}$ is the Ground truth RoI box for the entire frame.

The loss function can be determined by Equation 2:

$$L(p_i, p_i^*, \vec{b}_i, \vec{g}) = \sum_i -p_i^* \log p_i (S(x_i - x_g) + S(y_i - y_g) + S(w_i - w_g) + S(h_i - h_g))$$

where $p_i$ is the predicted probability for presence of Region of Interest (RoI) in the $i_{th}$ anchor box and the smooth loss function can be defined by Equation 3:

$$S(x) = \begin{cases} 0.5x^2 & |x| < 1 \\ |x| - 0.5 & \text{otherwise} \end{cases}$$

The left term in the loss function is the error in predicting the probability of the presence of a RoI, while the second term is the mismatch in the predicted Bounding Box (BBox). It should be noted that the second term vanishes when the ground truth indicates that there is no RoI in the anchor box.

The static Region of Interest (RoI) is independent of the action class. In another implementation, a dynamic Region of Interest (RoI), that is class dependent, is proposed by the CNNs. This takes the form of a rectangle enclosing the part of the image where the specific action is occurring. This increases the focus of the network and takes it a step closer to a local context-based action recognition.

Once a Region of Interest (RoI) has been identified, the frame feature can be extracted from within the RoI. These will yield a background independent frame digest. But this feature vector also needs to be a fixed size so that it can be fed into the Long Short Term Memory (LSTM). The fixed size can be achieved via RoI pooling. For RoI pooling, the RoI can be tiled up into 7×7 boxes. The mean of all feature vectors within a tile can then be determined. Thus, 49 feature vectors that are concatenated from the frame digest can be produced. The second Fully Connected (FC) layer 350 can provide additional non-linearity and expressive power to the machine, creating a fixed size frame digest that can be consumed by the LSTM 230.

At 470, successive foreground features can be fed into the Long Short Term Memory (LSTM) 230 to learn the temporal pattern. The LSTM 270 can be configured to recognize patterns in an input sequence. In video action recognition, there could be patterns within sequences of frames belonging to a single action, referred to as intra action patterns. There could also be patterns within sequences of actions, referred to as inter action patterns. The LSTM can be configured to learn both of these patterns, jointly referred to as temporal patterns. The Lone Short Term Memory (LSTM) analyzes a series of foreground features to recognize actions belonging to an overall sequence. In one implementation, the LSTM outputs an action class describing a recognized action associated with an overall process for each input it receives. In another implementation, each class action is comprised of sets of actions describing actions associated with completing an overall process. Each action within the set of actions can be assigned a score indicating a likelihood that the action matches the action captured in the input video frame. Each action may be assigned a score such that the action with the highest score is designated the recognized action class.

Foreground features from successive frames can be feed into the Long Short Term Memory (LSTM). The foreground feature refers to the aggregated feature vectors from within the Region of interest (RoI) rectangles. The output of the LSTM at each time step is the recognized action class. The loss for each individual frame is the cross entropy softmax loss over the set of possible action classes. A batch is defined as a set of three randomly selected set of twelve frame sequences in the video stream. The loss for a batch is defined as the frame loss averaged over the frame in the batch. The numbers twelve and three are chose empirically. The overall LSTM loss function is given by Equation 4:

$$L(B, \{S_1, S_2, \ldots, S_{\|B\|}\}) = \sum_{k=1}^{\|B\|} \sum_{t=1}^{\|S_k\|} \sum_{i=1}^{\|A\|} -\left(\frac{e^{a_{t_i}}}{\sum_{j=1}^{\|A\|} e^{a_{t_{ij}}}}\right) \log a_{t_i}^*$$

where B denotes a batch of $\|B\|$ frame sequences $\{S_1, S_2, \ldots, S_{\|K\|}\}$. $S_k$ comprises a sequence of $\|S_k\|$ frames, wherein in the present implementation $\|B\|=3$ and $\|S_k\|=12k$. A denotes the set of all action classes, $a_{t_i}$ denotes the $i_{th}$ action class score for the $t_{th}$ frame from LSTM and $a^*_{t_i}$ denotes the corresponding Ground Truth.

Referring again to FIG. 1, the machine learning back-end unit 135 can utilize custom labelling tools with interfaces optimized for labeling RoI cycles and action. The labelling tools can include both standalone application built on top of Open source Computer Vision (OpenCV) and web browser application that allow for the labeling of video segment.

Figure 5:
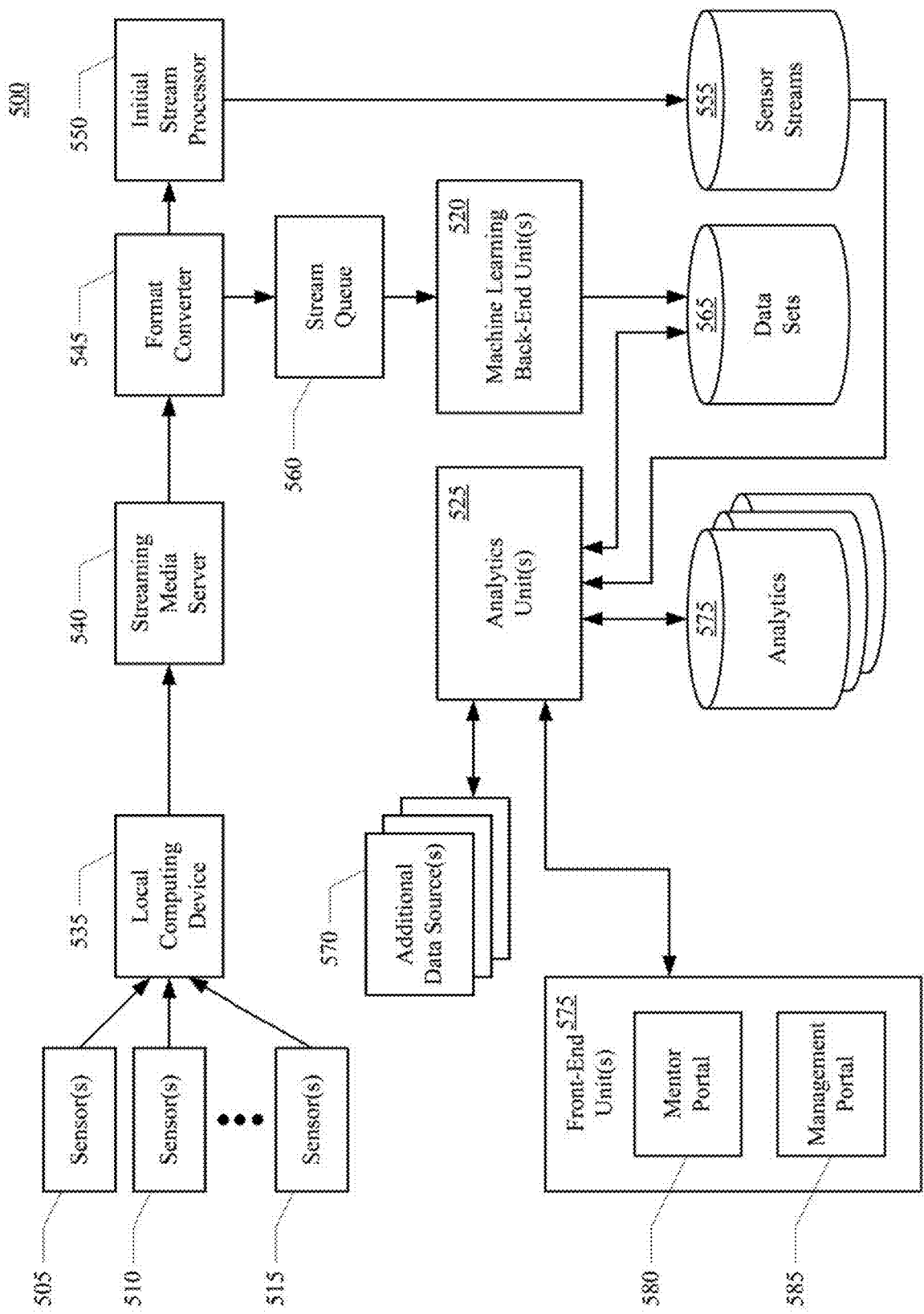
FIG. 5 shows an action recognition and analytics system, in accordance with aspects of the present technology.

Referring now to FIG. 5, an action recognition and analytics system, in accordance with aspect of the present technology, is shown. Again, the action recognition and analytics system 500 can be deployed in a manufacturing, health care, warehousing, shipping, retail restaurant, or similar context. The system 500 similarly includes one or more sensors 305-515 disposed at one or more stations, one or more machine learning back-end units 520, one or more analytics units 525, and one or more front-end units 530. The one or more sensors 505-515 can be coupled to one or more local computing devices 535 configured to aggregate the sensor data streams from the one or more sensors 503-515 for transmission across one or more communication links to a streaming media server 540. The streaming media server 540 can be configured to received one or more streams of sensor data from the one or more sensors 505-515. A formal converter 545 can be coupled to the streaming media server 540 to receive the one or more sensor data streams and convert the sensor data from one format to another. For example, the one or more sensors may generate Motion Picture Expert Group (MPEG) formatted (e.g., H.264) video sensor data, and the format converter 545 can be configured to extract frames of JPEG sensor data. An initial stream processor 550 can be coupled to the format convert 555. The initial stream processor 550 can be configured to segment the sensor data into predetermined chucks, subdivide the chunks into key frame aligned segment, and create per segment sensor data in one or more formats. For example, the initial stream processor 550 can divide the sensor data into five minute chunks, subdivide the chunks into key frame aligned segment, and convert the key frame aligned segments into MPEG, MPEG Dynamic Adaptive Streaming over Hypertext Transfer Protocol (DASH) format, and or the like. The initial stream processor 550 can be configured to store the sensor stream segments in one or more data structures for storing sensor streams 555. In one implementation, as sensor stream segments are received, each new segment can be appended to the previous sensor stream segments stored in the one or more data structures for storing sensor streams 555.

Figure 6:
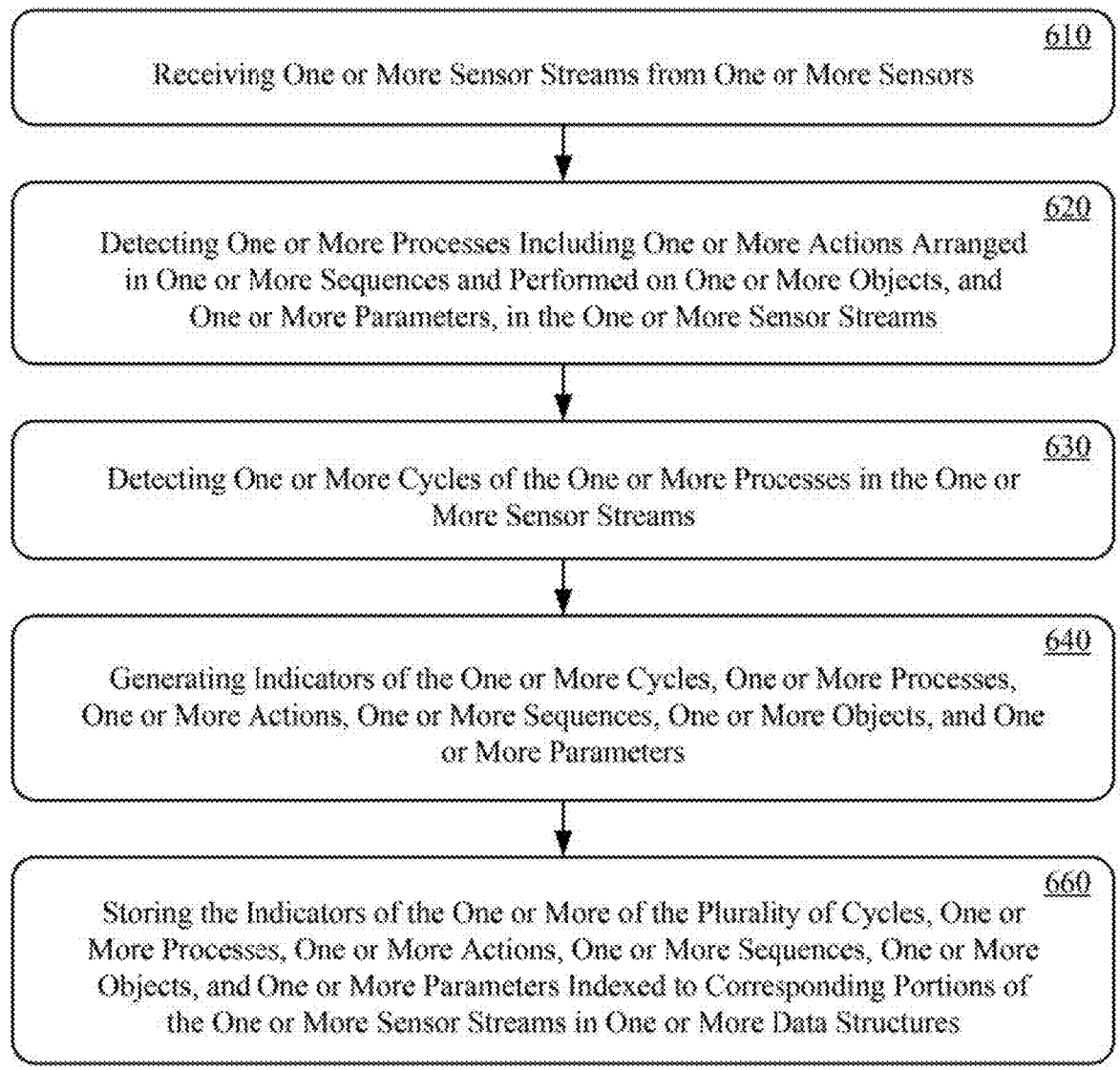
FIG. 6 shows an exemplary method of detecting actions, in accordance with aspects of the present technology.

A stream queue 560 can also be coupled to the format converter 545. The stream queue 560 can be configured to buffer the sensor data from the format converter 545 for processing by the one or more machine learning back-end units 520. The one or more machine learning back-end units 520 can be configured to recognize, in real time, one or more cycles, processes, actions, sequences, objects, parameters and the like in the sensor streams received from the plurality of sensors 505-515. Referring now to FIG. 6, an exemplary method of detecting actions, in accordance with aspects of the present technology, is shown. The action recognition method can include receiving one or more sensor streams from one or more sensors, at 610. In one implementation, one or more machine learning back-end units 520 can be configured to receive sensor streams from sensors 505-515 disposed at one or more stations.

At 620, a plurality of processes including one or mom actions arranged in one or more sequences and performed on one or more objects, and one or more parameters can be detected in the one or more sensor streams. At 630, one or more cycles of the plurality of processes in the sensor stream can also be determined. In one implementation, the one or more machine learning back-end units 520 can recognize cycles, processes, actions, sequences, objects, parameters and the life in sensor streams utilizing deep learning, decision tree learning, inductive logic programming, clustering, reinforcement learning, Bayesian networks, and or the like.

At 640, indicators of the one or more cycles, one or more processes, one or more actions, one or more sequences, one or more objects, and one or more parameters can be generated. In one implementation, the one or more machine learning back-end units 520 can be configured to generate indicators of the one or more cycles, processes, actions, sequences, objects, parameters and or the like. The indicators can include descriptions, identifier, values and or the like associated with the cycles, processes, actions, sequences, objects, and or parameters. The parameters can include, but is not limited to, time, duration, location (e.g., x, y, z, t), reach point, motion path, grid point, quantity, sensor identifier, station identifier, and bar codes.

At 650, the indicators of the one or more cycles, one or more processes, one or more actions, one or more sequences, one or more objects, and one or more parameters indexed to corresponding portions of the sensor streams can be stored in one or more data structures for storing data sets 565. In one implementation, the one or more machine learning back-end units 520 can be configured to store a data set including the indicators of the one or more processes, one or more actions, one or more sequences, one or more objects, and one or more parameters for each cycle. The data sets can be stored in one or more data structures for storing the data sets 565. The indicators of the one or more cycles, one or more processes, one or more actions, one or more sequences, one or more objects, and one or more parameters in the data sets can be indexed to corresponding portion of the sensor streams in one or more data structures for storing sensor streams 555.

In one implementation, the one or more streams of sensor data and the indicators of the one or more of the plurality of cycles, one or more processes, one or more actions, one or more sequences, one or more objects and one or more parameters indexed to corresponding portion of the one or more streams of sensor data can be encrypted when stored to protect the integrity of the streams of sensor data and or the data sets. In one implementation, the one or mote streams of sensor data and the indicators of the one or more of the plurality of cycles, one or more processes, one or more actions, one or more sequences, one or more objects and one or more parameters indexed to corresponding portion of the one or more streams of sensor data can be stored utilizing block chaining. The blockchaining can be applied across the cycles, sensor streams, stations, supply chain and or the like. The blockchaining can include calculating a cryptographic hash based on blocks of the data sets and or blocks of the streams of sensor data. The data sets, streams of sensor data and the cryptographic hash can be stored in one or more data structures in a distributed network.

Referring again to FIG. 5, the one or more analytics units 525 can be coupled to the one or more data structures for storing the sensor streams 555, one or more data structures for storing the data set 565, one or more additional sources of data 570, one or more data structures for storing analytics 575. The one or more analytics units 525 can be configured to perform statistical analysts on the cycle, process, action, sequence, object and parameter data in one or more data sets. The one or more analytics units 525 can also utilize additional data received from one or more additional data sources 570. The additional data sources 570 can include, but are not limited to, Manufacturing Execution Systems (MES), warehouse management system, or patient management system, accounting systems, robot datasheets, human resource records, bill of materials, and sales systems. Some examples of data that can be received from the additional data sources 570 can include, but is not limited to, time, date, shift, day of week, plant, factory, assembly line, sub-assembly line, building, room, supplier, work space, action capability, and energy consumption, ownership cost. The one or more analytics units 525 can be configured to utilize the additional data from one or more additional source of data 570 to update, correct, extend, augment or the like, the data about the cycles, processes, action, sequences, objects and parameters in the data sets. Similarly, the additional data can also be utilized to update, correct, extend, augment or the like, the analytics generate by the one or more analytics front-end units 525. The one or more analytics units 525 can also store trends and other comparative analytics utilizing the data sets and or the additional data, can use sensor fusion to merge data than multiple sensors, and other similar processing and store the results in the one or more data structures for storing analytics 575. In one implementation, one or more engines 170, such as the one or more machine learning back-end units 520 and or the one or more analytics units 525, can create a data structure including a plurality of data sets, the data sets including one or more indicators of at least one of one or more cycles, one or more processes, one or more actions, one or more sequences, one or more object and one or more parameters. The one or more engine 170 can build the data structure based on the one of one or more cycles, one or more processes, one or more actions, one or more sequences, one or more object and one or more parameters detected in the one or more sensor streams. The data structure definition, configuration and population can be performed in real time based upon the content of the one or more sensor streams. For example, Table 1 shows a table defined, configured and populated as the sensor streams are processed by the one or more machine learning back-end unit 520.

TABLE 1

ENTITY ID DATA STRUCTURE (TABLE 1)

| FRAME | HUMAN | HAND | ARM | LEG | MOTHER-BOARD | SCREW |
|---|---|---|---|---|---|---|
| 1 | Yes | Yes | Yes | Yes | YES | Yes |
| 2 | Yes | No | No | Yes | Yes | No |
| 3 | Yes | Yes | Yes | Yes | YES | Yes |

The data structure creation process can continue to expand upon the initial structure and or create additional data structures base upon additional processing of the one or more sensor streams.

In one embodiment, the status associated with entities is added to a data structure configuration (e.g., engaged in an action, subject to a force, etc.) based upon processing of the access information. In one embodiment, activity associated with the entities is added to a data structure configuration (e.g., engaged in an action, subject to a force, etc.) based upon processing of the access information. One example of entity status data set created from processing of above entity ID data set (e.g., motion vector analysis of image object, etc.) is illustrated in Table 2.

TABLE 2

ENTITY STATUS DATA STRUCTURE (TABLE 2)

| FRAME | HAND MOVING | ARM MOVING | LEG MOVING | HUMAN MOVING |
|---|---|---|---|---|
| 1 | Yes | Yes | No | Yes |
| 2 | No | No | Yes | No |
| 3 | Yes | Yes | Yes | Yes |

In one embodiment, a third-party data structure as illustrated in Table 3 can be accessed.

TABLE 3

OSHA DATA STRUCTURE (TABLE 3)

| ACTIVITY | SAFE TO MOVE LEG | SAFE TO MOVE HAND |
|---|---|---|
| SCREWING TO MOTHERBOARD | No | Yes |
| LIFTING HOUSING | Yes | Yes |

In one embodiment, activity associated with entitles is added to a data structure configuration (e.g., engaged in an action, subject to a force, etc.) based upon processing of the access information as illustrated in Table 4.

TABLE 4

ACTIVITY DATA STRUCTURE (TABLE 4)

| FRAME | SCREWING TO MOTHERBOARD | HUMAN ACTION SAFE | MOTHERBOARD COMPLETE |
|---|---|---|---|
| 1 | Yes | Yes | Yes |
| 2 | No | NA | NO |
| 3 | Yes | NO | Yes |

Table 4 is created by one or more engines 170 based on further analytics/processing of info in Table 1, Table 2 and Table 3. In one example, Table 4 is automatically configured to have a column for screwing to motherboard. In frames 1 and 3 since hand is moving (see Table 2) and screw present (see Table 1), then screwing to motherboard (see Table 3). In frame 2, since hand is not moving (see Table 2) and screw not present (see Table 1), then no screwing to motherboard (see Table 3).

Table 4 is also automatically configured to have a column for human action sale. In frame 1 since leg not moving in frame (see Table 2) the worker is safely (see Table 3) standing at workstation while engage in activity of screwing to motherboard. In frame 3 since leg moving (see Table 2) the worker is not safely (see Table 3) standing at workstation while engage in activity of screwing to motherboard.

The one or more analytics units 525 can also be coupled to one or more front-end units 580. The one or more front-end units 575 can include a mentor portal 580, a management portal 585, and other similar portals. The mentor portal 550 can be configured for presenting feedback generated by the sine or more analytics units 535 and or the one or more front-end units 575 to one or more actors. For example, the mentor portal 580 can include a touch screen display for indicating discrepancies in the processes, actions, sequences, objects and parameters at a corresponding station. The mentor portal 580 could also present training content generated by the one or more analytics units 525 and or the one or more front-end units 575 to an actor at a corresponding station. The management port 585 can be configured to enable searching of the one or more data structures storing analytics, data sets and sensor streams. The management port 585 can also be utilized to control operation of the one or more analytics units 525 for such functions as generating training content, creating work charts, performing line balancing analysis, assessing ergonomics, creating job assignments, performing causal analysis, automation analysis, presenting aggregated statistics, and the like.

The action recognition and analytics system 500 can non-intrusively digitize processes, actions, sequences, objects, parameters and the like performed by numerous entities, including both humans and machines, using machine learning. The action recognition and analytics system 500 enables human activity to be measured automatically, continuously and at scale. By digitizing the performed processes, actions, sequences, objects, parameters, and the like, the action recognition and analytics system 500 can optimize manual and or automatic processes. In one instance, the action recognition and analytics system 500 enables the creation of a fundamentally stew data set of human activity. In another instance, the action recognition and analytics system 500 enables the creation of a second fundamentally new data set of man and machine collaborating in activities. The data set from the action recognition and analytics system 500 includes quantitative data, such as which actions were performed by which person, at which station, on which specific part, at what time. The data set can also include judgements based on performance data, such as does a given person perform better or worse that average. The data set can also include inferences based on an understanding of the process, such as did a given product exited the assembly line with one or more incomplete tasks.

Figure 7:
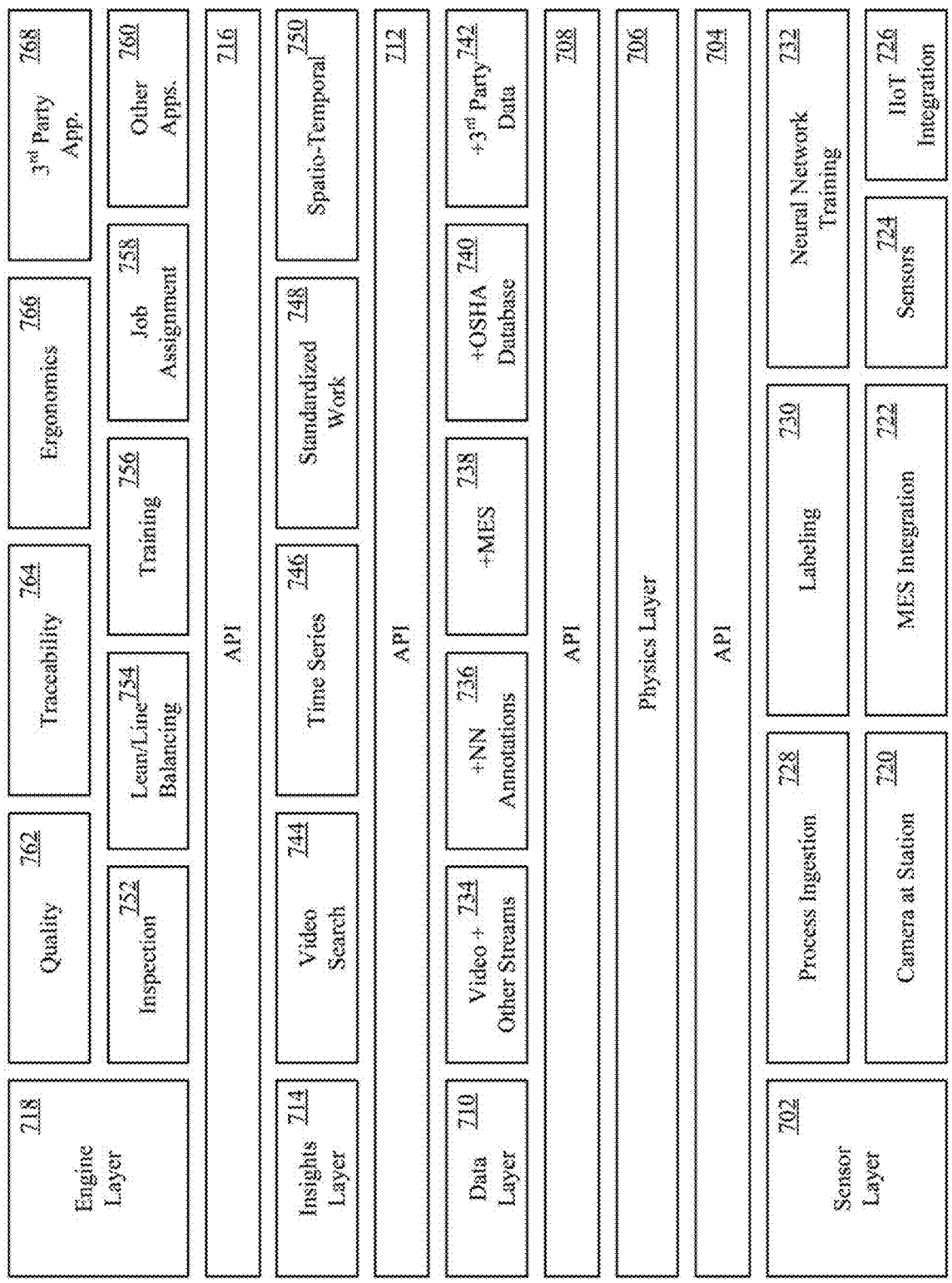
FIG. 7 shows an action recognition and analytics system, in accordance with aspects of the present technology.

Referring now to FIG. 7, an action recognition and analytics system, in accordance with aspects of the present technology, is shown. The action recognition and analytics system can include a plurality of sensor layers 702, a first Application Programming Interface (API) 704, a physics layer 706, a second API 708, a plurality of data 710, a third API 712, a plurality of insights 714, a fourth API 716 and a plurality of engine layers 718. The sensor layer 702 can include, for example, cameras at one or more stations 720, MES stations 722, sensors 724, IIoT integrations 726, process ingestion 728, labeling 730, neural network training 732 and or the like. The physics layer 706 captures data from the sensor layer 702 to passes it to the data layer 710. The data layer 710, can include but not limited to, video and other streams 734, +NN annotations 736, +MES 738, +OSHA database 740, and third-party data 742. The insights layer 714 can provide for video search 744, time series data 746, standardized work 748, and spatio-temporal 842. The engine layer 718 can be utilized tor inspection 752, lean/line balancing 754, training 755, job assignment 758, other applications 760, quality 763, traceability 764, ergonomics 766, and third party applications 768.

Figure 8:
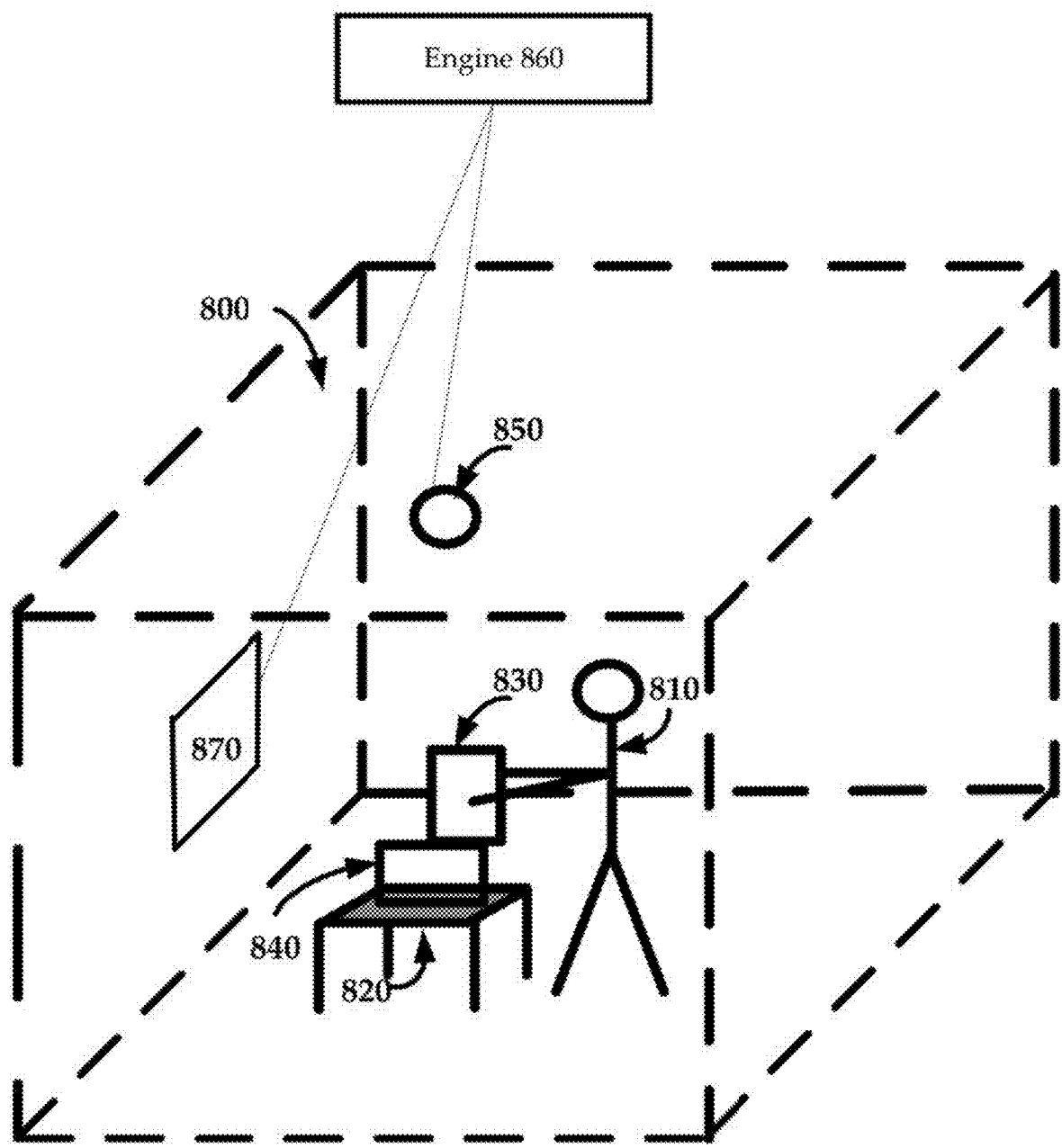
FIG. 8 shows an exemplary station, in accordance with aspects of the present technology

Referring now to FIG. 8, an exemplary station, in accordance with aspects of the present technology, is shown. The station 800 is an areas associated with one or more cycles, processes, actions, sequences, objects, parameters and or the like, herein also referred to as activity. Information regarding a station can be gathered and analyzed automatically. The information can also be gathered and analyzed in real time. In one exemplary implementation, an engine participates in the information gathering and analysis. The engine can use Artificial Intelligence to facilitate the information gathering and analysis. It is appreciated there can be many different types of stations with various associated entities and activities. Additional descriptions of stations, entities, activities, information gathering, and analytics are discussed in other sections of this detailed description.

A station or area associated with an activity can include various entities, some of which participate in the activity within the area. An entity can be considered an actor, an object, and so on. An actor can perform various actions on an object associated with an activity in the station. It is appreciated a station can be compatible with various types of actors (e.g., human, robot, machine, etc.). An object can be a target object that is the target of the action (e.g., thing being acted on, a product, a tool etc.). It is appreciated that an object can be a target object that is the target of the action and then can be various types of target objects (e.g., component of a product or article of manufacture, an agricultural item, part of a thing or person being operated on, etc.). An object can be a supporting object that supports (e.g., assists, facilitates, aids, etc.) the activity. There can be various types of supporting objects, including load bearing components (e.g., a work bench, conveyor belt, assembly line, table top etc.), a tool (e.g., drill, screwdriver, lathe, press, etc.), a device that regulates environmental conditions (e.g., heating ventilating and air conditioning component, lighting component, fire control system, etc.), and so on. It is appreciated there can be many different types pf stations with a various entities involved with a variety of activities. Additional descriptions of the station, entities, and activities are discussed in other sections of this detailed description.

The station 800 can include a human actor 810, supporting object 820, and target objects 830 and 840. In one embodiment, the human actor 810 is assembling a product that includes target objects 830, 840 while supporting object 820 is facilitating the activity. In one embodiment target objects 830, 840 are portions of a manufactured product (e.g., a motherboard and a housing of an electronic component, a frame and a motor of a device, a first and a second structural member of an apparatus, legs and seat portion of a chair, etc.). In one embodiment, target objects 830, 840 are items being loaded in a transportation vehicle. In one embodiment, target objects 830, 840 are products being stocked in a retail establishment. Supporting object 820 is a load bearing component (e.g., a work bench, a table, etc.) that holds target object 840 (e.g., during the activity, alter the activity, etc.). Sensor 850 senses information about the station (e.g., actors, objects, activities, actions, etc.) and forwards the information to one or more engines 860. Sensor 850 can be similar to sensor 135. Engine 860 can include a machine learning back end component, analytics, and front end similar to machine learning back end unit 180, analytics unit 190, and front end 190. Engine 860 performs analytics on the information and can forward feedback to feedback component 870 (e.g., a display, speaker, etc.) that conveys the feedback to human actor 810.

Figure 9:
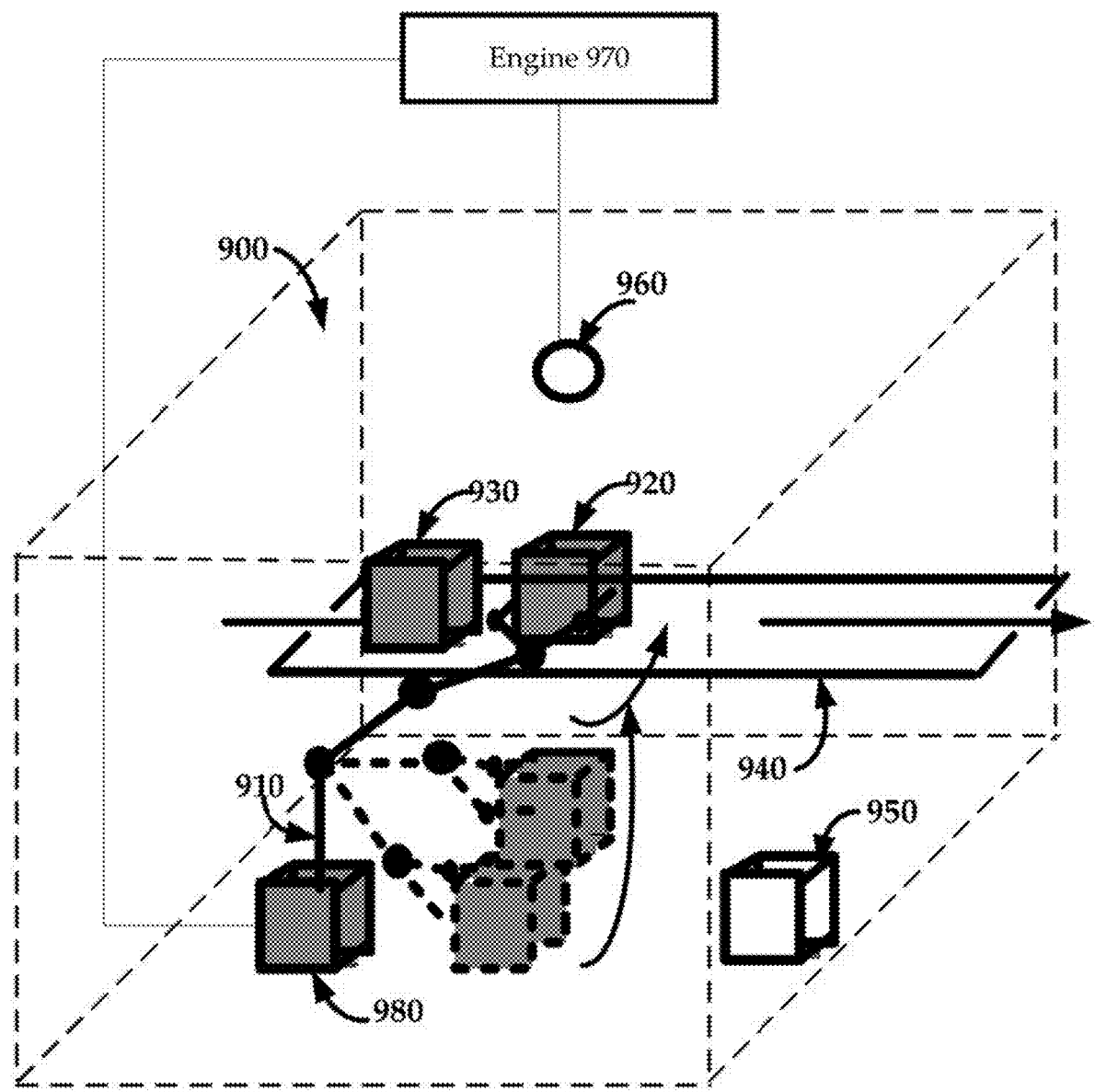
FIG. 9 shows an exemplary station, in accordance with aspects of the present technology

Referring now to FIG. 9, an exemplary station, in accordance with aspects of the present technology, is shown. The station 900 includes a robot actor 910, target objects 920, 930, and supporting objects 940, 950. In one embodiment, the robot actor 910 is assembling target objects 920, 930 and supporting objects 940, 950 are facilitating the activity. In one embodiment, target objects 920, 930 are portions of a manufactured product. Supporting object 940 (e.g., an assembly line, a conveyor belt, etc.) holds target objects 920, 930 during the activity and moves the combined target object 920, 930 to a subsequent station (not shown) after the activity. Supporting object 940 provides area support (e.g., lighting, fan temperature control, etc.). Sensor 960 senses information about the station (e.g., actors, objects, activities, actions, etc.) and forwards the information to engine 970. Engine 970 performs analytics on the information and forwards feedback to a controller 980 that controls robot 910. Engine 970 can be similar to engine 170 and sensor 960 can be similar to sensor 135.

A station can be associated with various environments. The station can be related to an economic sector. A first economic sector can include the retrieval and production of raw materials (e.g., raw food, feel, minerals, etc.). A second economic sector can include the transformation of raw or intermediate materials into goods (e.g., manufacturing products, manufacturing steel into cars, manufacturing textiles into clothing, etc.). A third sector can include the supply and delivery of services and products (e.g., an intangible aspect in its own right, intangible aspect as a significant element of a tangible product, etc.) to various parties (e.g., consumers, businesses, governments, etc.). In one embodiment, the third sector can include sub sectors. One sub sector can include information and knowledge-based services. Another sub sector can include hospitality and human services. A station can be associated with a segment of an economy (e.g., manufacturing, retail, warehousing, agriculture, industrial, transportation, utility, financial, energy, healthcare, technology, etc,). It is appreciated there can be many different types of stations and corresponding entities and activities. Additional descriptions of the station, entities, and activities are discussed in other sections of this detailed description.

Figure 10:
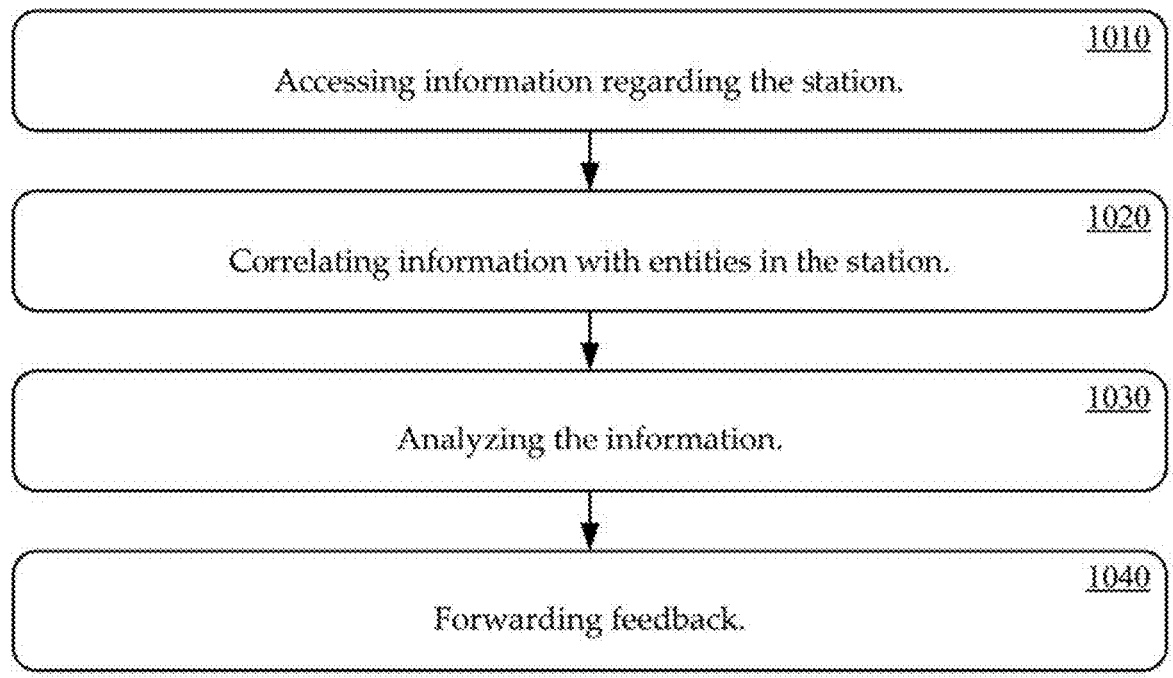
FIG. 10 shows an exemplary station activity analysis method, in accordance with one embodiment.

In one embodiment, station information is gathered and analyzed. In one exemplary implementation, an engine (e.g., an information processing engine, a system control engine, an Artificial Intelligence engine, etc.) can access information regarding the station (e.g., information on the entities, the activity, the action, etc.) and utilizes the information to perform various analytics associated with the station. In one embodiment, engine can include a machine learning back end unit, analytics unit, front end unit, and data storage unit similar to machine learning back end 180, analytics 185, front end 190 and data storage 175. In one embodiment, a station activity analysis process is performed. Referring now to FIG. 10, an exemplary station activity analysis method, in accordance with one embodiment, is shown.

At 1010, information regarding the station is accessed. In one embodiment, the information is accessed by an engine. The information can be accessed in real time. The information can be accessed from monitors/sensors associated with a station. The information can be accessed from an information storage repository. The information can include various types of information (e.g., video, thermal, optical, etc.). Additional descriptions of the accessing information are discussed in other sections of this detailed description At 1020, information is correlated with entities in the station and optionally with additional data sources. In one embodiment, the information the correlation is established at least in part by an engine. The engine can associate the accessed information with an entity in a station. An entity can include an actor, an object, and so on. Additional descriptions of the correlating information with entities are discussed in other sections of this detailed description.

At 1030, various analytics are performed utilizing the accessed information at 1010, and correlations at 1020. In one embodiment, an engine utilizes the information to perform various analytics associated with station. The analytics can be directed at various aspects of an activity (e.g., validation of actions, abnormality detection, training, assignment of actor to an action, tracking activity on an object, determining replacement actor, examining actions of actors with respect to an integrated activity, automatic creation of work charts, creating ergonomic data, identify product knitting components, etc.) Additional descriptions of the analytics are discussed in other sections of this detailed description.

At 1040, optionally, results of the analysis can be forwarded as feedback. The feedback can include directions to entities in the station. In one embodiment, the information accessing, analysis, and feedback are performed to real time. Additional descriptions of the station, engine, entities, activities, analytics and feedback are discussed in other sections of this detailed description.

It is also appreciated that accessed information can include general information regarding the station (e.g., environmental information, generic identification of the station, activities expected in station, a golden rule for the station, etc.). Environmental information can include ambient aspects and characteristics of the station (e.g., temperature, lighting conditions, visibility, moisture, humidity, ambient aroma, wind, etc.).

It also appreciated that some of types of characteristics or features can apply to a particular portion of a station and also the general environment of a station. In one exemplary implementation, a portion of a station (e.g., work bench, floor area, etc.) can have a first particular visibility level and the ambient environment of the station can have a second particular visibility level. It is appreciated that some of types of characteristics or features can apply to a particular entity in a station and also the station environment. In one embodiment, an entity (e.g., a human, robot, target object, etc.) can have a first particular temperature range and the station environment can have a second particular temperature range.

The action recognition and analytics system 100, 500 can be utilized for process validation, anomaly defection and/or process quality assurance in real time. The action recognition and analytics system 100, 500 can also be utilized for real time contextual training. The action recognition and analytics system 100, 500 can be configured for assembling training libraries from video clips of processes to speed new product introductions or onboard new employees. The action recognition and analytics system 100, 500 can also be utilized for line balancing by identifying processes, sequences and/or actions to move among stations and implementing lean processes automatically. The action recognition and analytics system 100, 500 can also automatically create standardized work charts by statistical analysis of processes, sequences and actions. The action recognition and analytics system 100, 500 can also automatically create birth certificate videos for a specific unit. The action recognition and analytics system 100, 500 can also be utilized for automatically creating statistically accurate ergonomics data. The action recognition and analytics system 100, 500 can also be utilized to create programmatic job assignments based on skills, tasks, ergonomics and time. The action recognition and analytics system 100, 500 can also be utilized for automatically establishing traceability including for causal analysis. The action recognition and analytics system 100, 500 can also be utilized for kitting products, including real time verification of packing or unpacking by action and image recognition. The action recognition and analytics system 100, 500 can also be utilized to determine the best robot to replace a worker when ergonomic problems are identified. The action recognition and analytics system 100, 500 can also be utilized to design an integrated line of humans and cobot and/or robots. The action recognition and analytics system 100, 500 can also be utilized for automatically programming robots based on observing non-modeled objects in the work space.

Embodiments of the present invention implement a method and system for automatically creating statistically accurate ergonomics data. Embodiments of the present invention implement a method for gathering data using modern and innovative techniques to implement a much more robust and complete dataset. Embodiments of the present invention implement an accurate dataset, that is not dependent upon whether people are conscious of being observed while performing their work. Embodiments of the present invention implement a method and a system for automatically creating statistically accurate ergonomics data.

Embodiments of the present invention implement a technology that non-intrusively digitizes actions performed by both humans and machines using machine learning. By digitizing actions performed, embodiments of the present invention convert them into data that can be applied for process optimization. Embodiments of the present invention uses technology that enables human activities to be measured automatically, continuously and at scale.

While one initial focus is manufacturing, the technology is applicable to human activity in any setting. Embodiments of the present invention enable the creation of a fundamentally new dataset of human actions. This dataset includes quantitative date (which actions were performed by which person, at which station, on which specific part, at what time); judgements based on performance data (person X performs better/worse than average); and inferences based on an understanding of the process (product Y exited the line with incomplete tasks). This dataset enables embodiments of the present invention to fundamentally re-imagine many of the techniques used to optimize manual and automated processes from manufacturing to the service industry.

Beyond the measurement of actions, embodiments of the present invention implement a system that is capable of performing the aforementioned process validation in seconds, and that is, identifying which activity is being performed as well as the movements of the actors as they perform the activity, able to determine whether or not the action conforms to the correct process, and communicate the information about process adherence/deviation back to the actor performing the action or to other interested parties. This further expands the range of business applications to which embodiments of the present invention can be applied, either new or re-imagined.

Embodiments of the present invention enable a number of applications by instrumenting a workstation, recording data (e.g., video, audio, thermal, vibration) from this workstation, labeling the actions in this data, building machine learning models, training these models to find the best predictor, and then inferring the actions observed in the data feed(s), possibly in real-time driving business processes with this data.

Embodiments of the present invention can identify spatio-temporal information of the worker performing his or her required tasks. In one embodiment, since the camera is not always placed orthogonal to the worker, the data it captures can be distorted, based on the camera's viewpoint. Using camera coordinates and image projection techniques, the worker's hand coordinates (x, y, z) can be established accurately. Embodiments of the present invention can then continuously collect spatial data of worker's body parts (e.g., hands) as she executes tasks on the assembly line. In more sophisticated analyses, (e.g., 3D, x, y, z, roll, pitch, yaw) data is collected along with a synchronized time stamp. With this spatio-temporal data, embodiments of the present invention can determine and output, reach studies using statistical analysis overtime (distance), motion studies using statistical analysis over time (distance and frequency), repetitive motion analysis studies (distance, frequency and count), torque and load studies (force, frequency and count), and reports identifying unsafe conditions that are created by integrating the present technologies spatio-temporal data with OSHA ergonomic rules (reach, repetition frequency, etc.). In one embodiment, these reports can be delivered on a scheduled or an ad hoc basis when certain pre-specified conditions established by regulatory requirements or scientific work are identified.

As stated earlier, current techniques require manual generation of time and motion data, a process that is fundamentally limiting and flawed. In contrast, by generating large volumes of data and non-dimensionalizing the data in new and creative ways, embodiments of the present invention enable analysis of repetitive motion injury. This enables embodiments of the present invention to, based on a large data set, uniquely, provide insights into the inherent safety of the work environment for workers and address a top priority for most manufacturers.

Embodiments of the present Invention collect time and motion data as described above. In reach studies, embodiments of the present invention plot all the points it has observed, creating a spatio-temporal dataset of places in the workspace that the operator reaches out to. Additionally, similar representations of two-dimensional projections of the three-dimensional data can be constructed to analyze worker movements in the horizontal and vertical planes. Further, embodiments of the present invention can produce continuous motion data from worker's hands starting position (e.g., x1, y1, z1) to ending position (e.g., x2, y2, z2). This data can be analyzed over a time-period for repetitive motions to identify ergonomic issues developing across long periods.

In this manner, embodiments of the present invention are directed to providing an ergonomic correct environment. In one embodiment, activity of a human actor is monitored and analyzed. The analysis can have a predictive element/nature (e.g. predict movement/result to determine if a dangerous condition/collision is going to happen before bad event happens). Feedback on a corrective action can be provided to the actors (e.g., an alarm of collision/dangerous condition, an is order for robot to stop/take evasive measure, etc.). Compliance oi the actor with safety guidelines can be checked and alarm forwarded if not.

In one embodiment, the present invention is implemented as a method that includes accessing information associated with a first actor, including sensed activity information associated with an activity space, analyzing the activity information, including analyzing activity of the first actor with respect to ergonomic factors, and forwarding feedback on the results of the analysis, wherein the results includes identification of ergonomically problematic activities.

Figure 11:
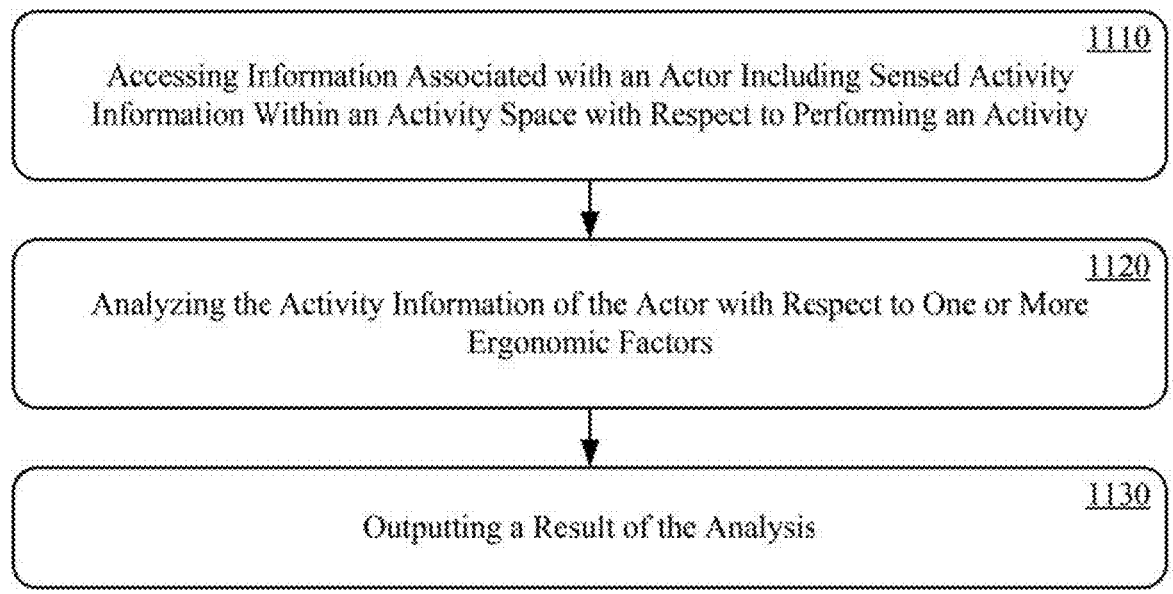
FIG. 11 shows a machine learning based ergonomics method, in accordance with aspects of the present technology.

Referring now to FIG. 11, a machine learning based ergonomics method, in accordance with aspects of the present technology, is shown. The method can include accessing information associated with an actor including sensed activity information within an activity space with respect to performing an activity, at 1110. At 1120, the activity information of the actor can be analyzed with respect to one or more ergonomic factors. At 1130, the results of the analysis can be output.

Figure 12:
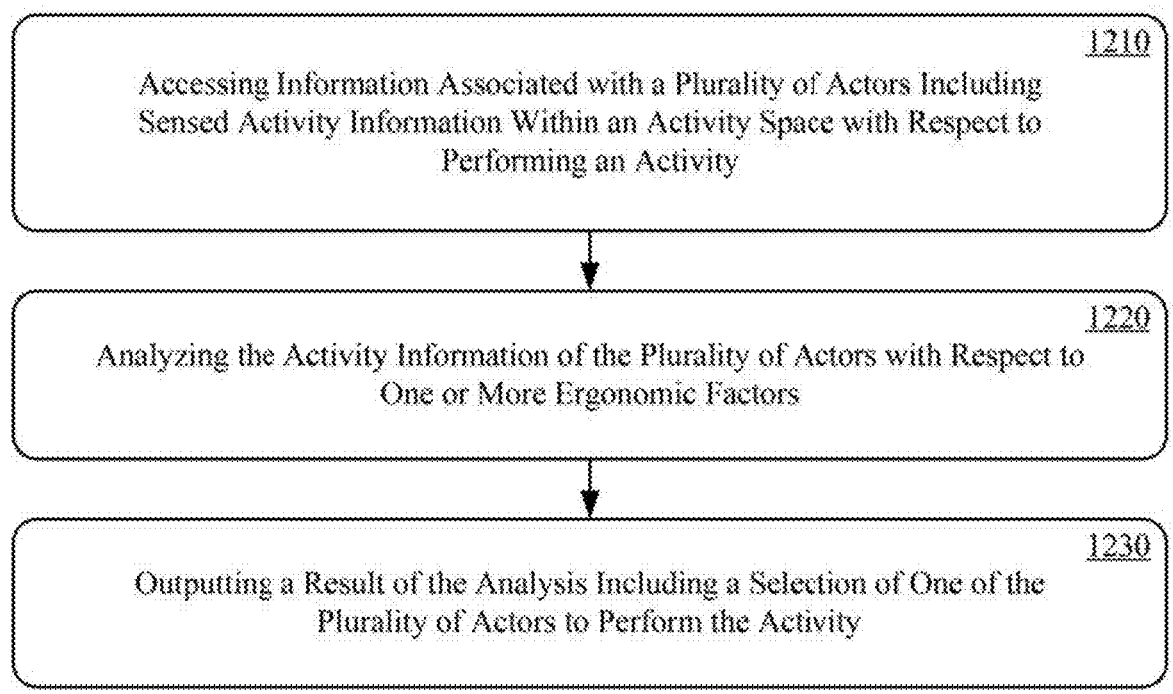
FIG. 12 shows a machine learning based ergonomics method, in accordance with aspects of the present technology.

Referring now to FIG. 12, a machine learning based ergonomics method, in accordance with aspects of the present technology, is shown. The method can include accessing information associated with a plurality of actors including sensed activity information within an activity space with respect to performing one or more activities, at 1210. At 1220, the activity information of the plurality of actors can be analyzed with respect to one or more ergonomic factors. At 1230, a result of the analysis including a selection of one of the plurality of actors to perform the activity can be output.

Figure 13:
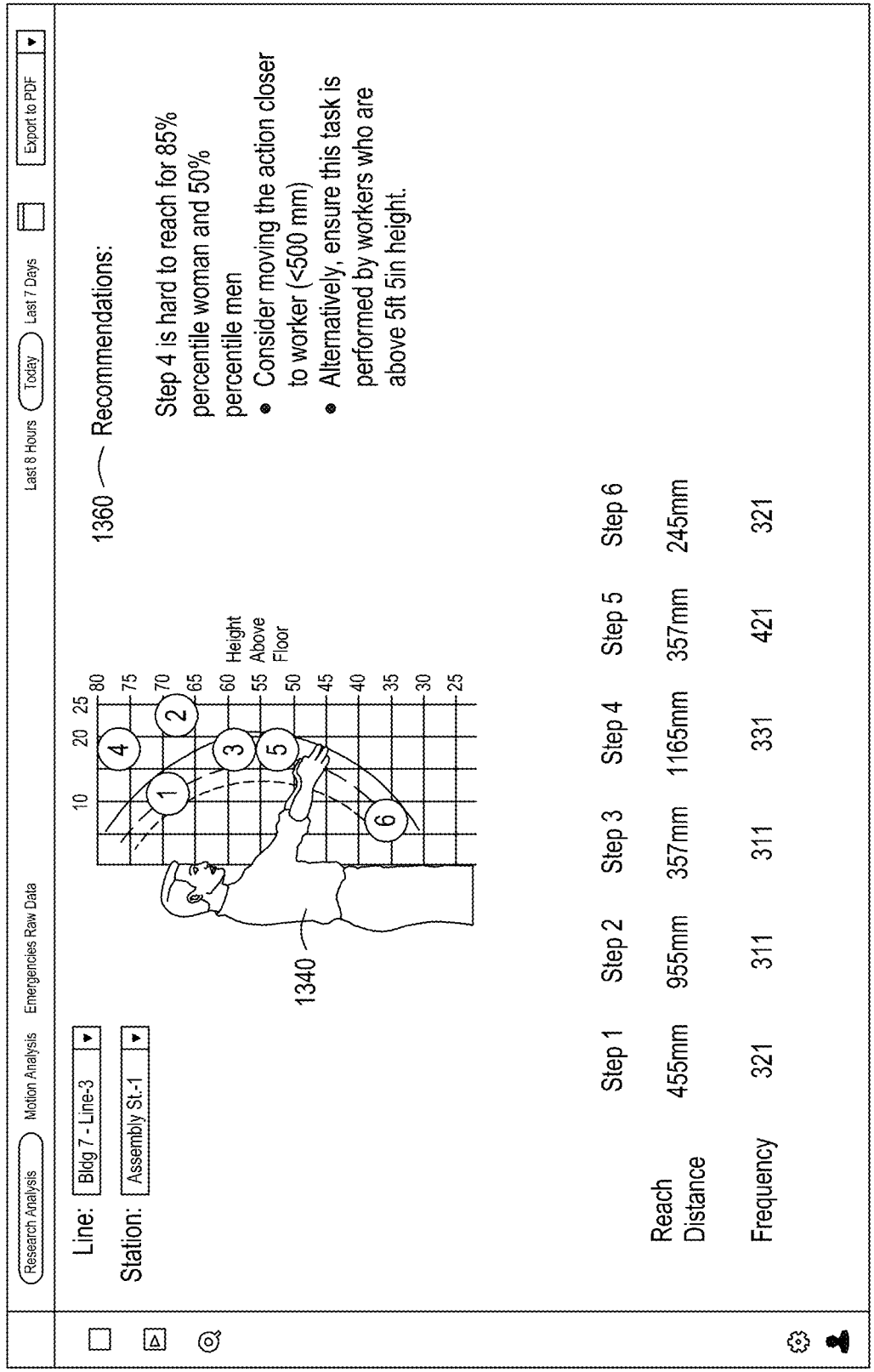
FIG. 13 shows an exemplary ergonomics reach diagram, in accordance with aspects of the present technology.

Referring now to FIG. 13, a side view of an ergonomics reach data diagram is shown on a graphical user interface (GUI), in accordance with aspects of the present technology. The reach data diagram shows six locations, numbered one through six, of reaching tasks that are performed by the depicted worker 1340. The depicted worker can be male or female, tail or short and represent the diversity of humans. The GUI ergonomics reach data diagram graphs distances in both the vertical dimension and the horizontal dimension using a grid as shown. Based upon gathered data, the deep learning system first identifies the reach points, then performs reach analysis and generates the recommendations 1360. As shown, exemplary recommendations can include identifying steps which are hard-to-reach for 85 percent of women and 50 percent of men. As shown, exemplary recommendations include moving the action (e.g., step 4) closer to the worker, or alternatively, ensuring the task is performed by workers who are above 5'5" in height.

Figure 14:
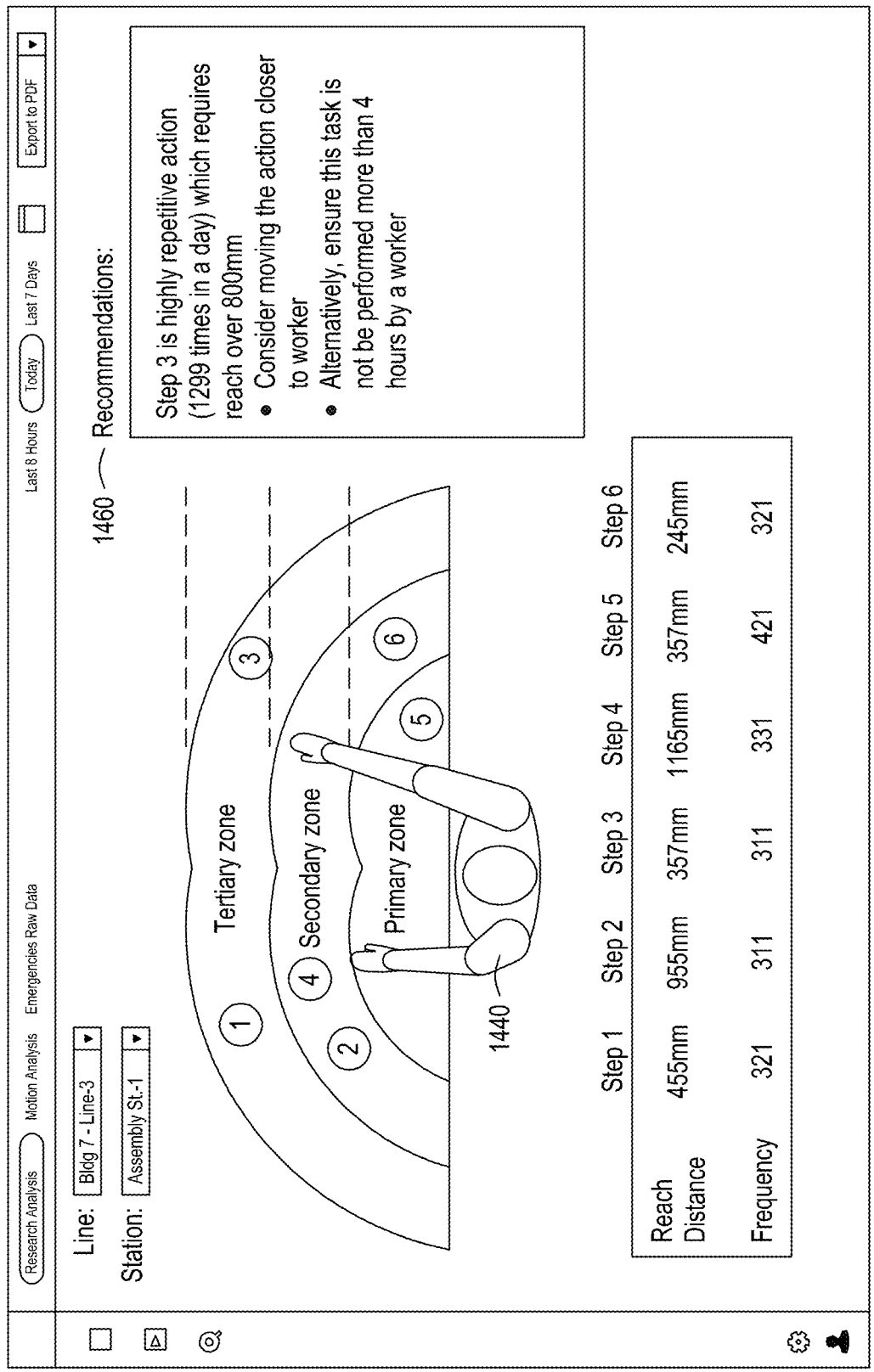
FIG. 14 shows an exemplary ergonomics reach diagram, in accordance with aspects of the present technology.

Referring now to FIG. 14, a top down view of an ergonomics reach data diagram is shown on a graphical user interface (GUI), in accordance with aspects of the present technology. The reach data diagram shows six locations, numbered one through six, of reaching tasks that are performed by the depicted worker 1440. The depicted worker can be male or female. Based upon gathered data, the deep learning system performs reach analysis and generates the recommendations 1460. As shown, exemplary recommendations can include identifying steps which are highly repetitive actions, and which require a reach over 800 mm. As shown, exemplary recommendations include moving the action (e.g., step 3) closer to the worker, or alternatively, ensuring the task is not performed more than four hours by a worker.

Figure 15:
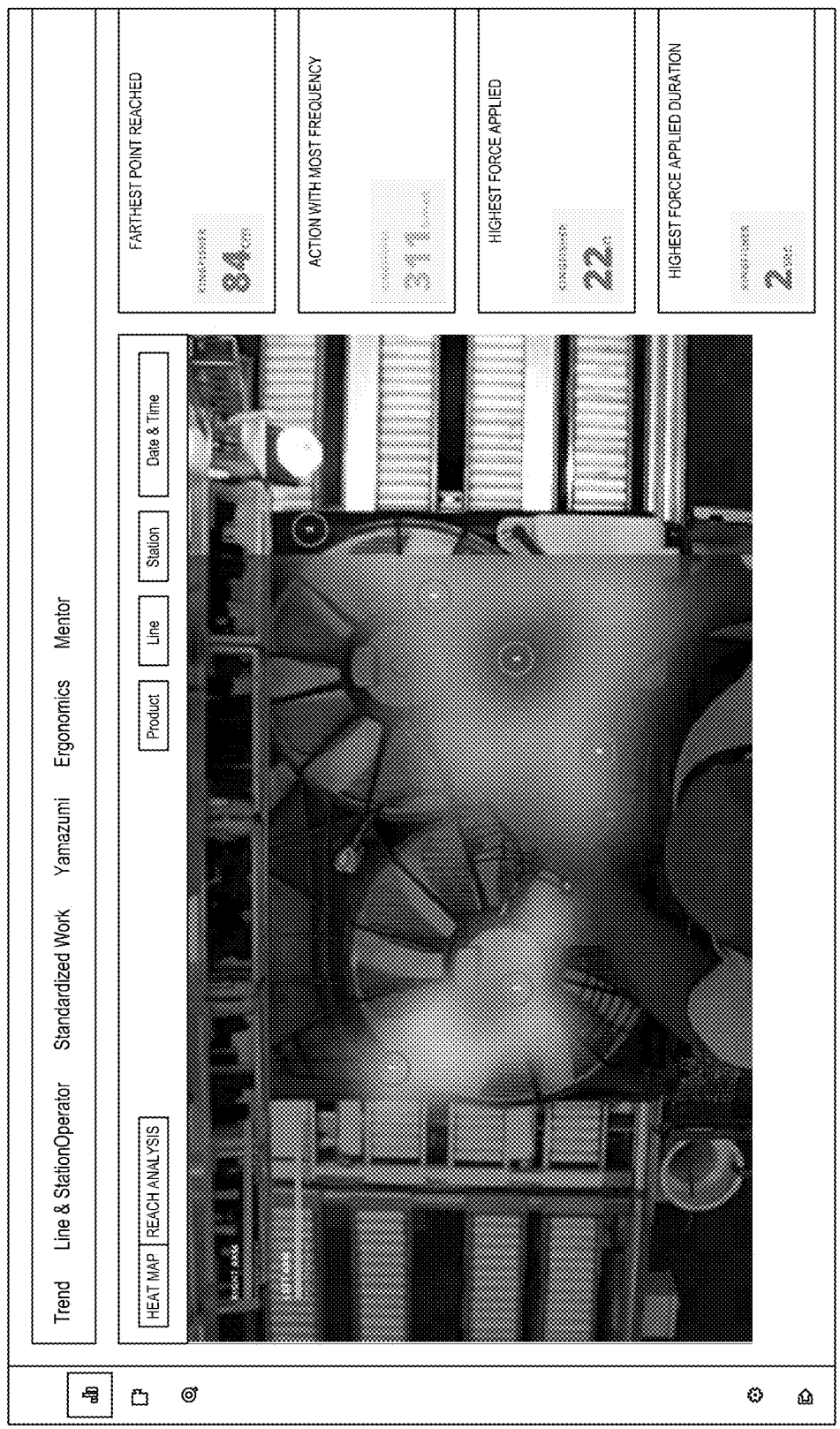
FIG. 15 shows an exemplary ergonomics reach diagram, in accordance with aspects of the present technology.

Referring now to FIG. 15, a top down view of an ergonomics reach data diagram is shown on a graphical user interface (GUI), in accordance with aspects of the present technology. The reach data diagram shows a heat map of reaching tasks that are performed by the depicted worker. Based upon gathered data, the deep learning system performs reach analysis and generates ergonomics data that can include metrics such as furthest point reached, action with most frequency, highest force applied, highest for applied duration and or the like along with the corresponding portions of a sensor stream overlaid with the heat map of the reaching tasks performed by the worker.

Referring now to FIG. 16, an exemplary simple raw data table produced in accordance with aspects of the present technology is shown. The deep learning system of the present technologies can produce continuous motion data from worker's hands starting position (e.g., x, y, z) to ending position (e.g., x1, y1, z1). This data can be analyzed over a time-period for repetitive motions to identify ergonomic issues developing across long periods. This is shown by the dates and times, identified actions, starting coordinates, and in coordinates, the weight of the item, and the movement distance.

In this manner, aspects of the present technology implement a method comprising, accessing information associated with a first actor, including sensed activity information associated with an activity space, analyzing the activity information, including analyzing activity of the first actor with respect to ergonomic factors, and forwarding feedback on the results of the analysis, wherein the results includes identification of economically problematic activities.

In one embodiment, the information is from sensors monitoring a work space in real time, wherein the information is accessed and analyzed in real time, and the feedback is forwarded in real time. In one embodiment, the analyzing comprises: comparing information associated with activity of the first actor within the activity space with identified representative actions, and identifying a deviation between the activity of the first actor and the representative standard.

In one embodiment, the analyzing comprises: determining if the deviation associated with a respective one of the plurality of actors is within an acceptable threshold (limit/parameter, measurement), and identifying the respective one of the plurality of other actors as a potential acceptable candidate to be the replacement actor when the deviation associated with a respective one of the plurality of actors is within the acceptable threshold. In one embodiment, the analysis includes creating a spatio-temporal dataset of locations in the workspace the first actor activity involves.

In one embodiment, the analyzing includes automated artificial intelligence analysis. In one embodiment, the sensed activity information is associated with a grid within the activity space. In one embodiment, the first actor is a human. In one embodiment, the sensed activity information further includes a second actor, wherein the first actor is a device and the second actor is a human.

Aspects of the technology implement a method comprising: accessing information associated with a first actor, including sensed activity information within an activity space with respect to performing an activity, analyzing the activity information, including analyzing activity of the first actor and analyzing activity of the second actor, and forwarding feedback on the results of the analysis, wherein the results include a identification of a selection between the first actor and the second actor.

In one embodiment, the accessing information includes continual spatial data associated with the first actor's activities. In one embodiment, the analysis includes the distance a part of the first actor moves (reach/bend/lean/(leg or arm) extension study using statistical analysis over time). In one embodiment, the analysis includes the distance and frequency a part of the first actor moves (motion/action study using statistical analysis over time). In one embodiment, the analysts includes the distance, frequency, and count a part of the first actor move (repetitive motion/action study using statistical analysis over time).

In one embodiment, the analysis includes comparison with safety standards (OSHA-—is safety equipment being used/worn correctly). In one embodiment, the analysis includes consideration of forces on the first actor (weight/torque/load). In one embodiment, the analysis includes consideration of characteristics of the first actor (height/weight/strength). In one embodiment, the feedback is provided in real time and on an ad hoc basis. In one embodiment, the ad hoc basis corresponds to safety regulations. In one embodiment, the analysis and feedback includes identification of omitted safety activity (sweep floor, wash, food prep, etc.).

Figure 17:
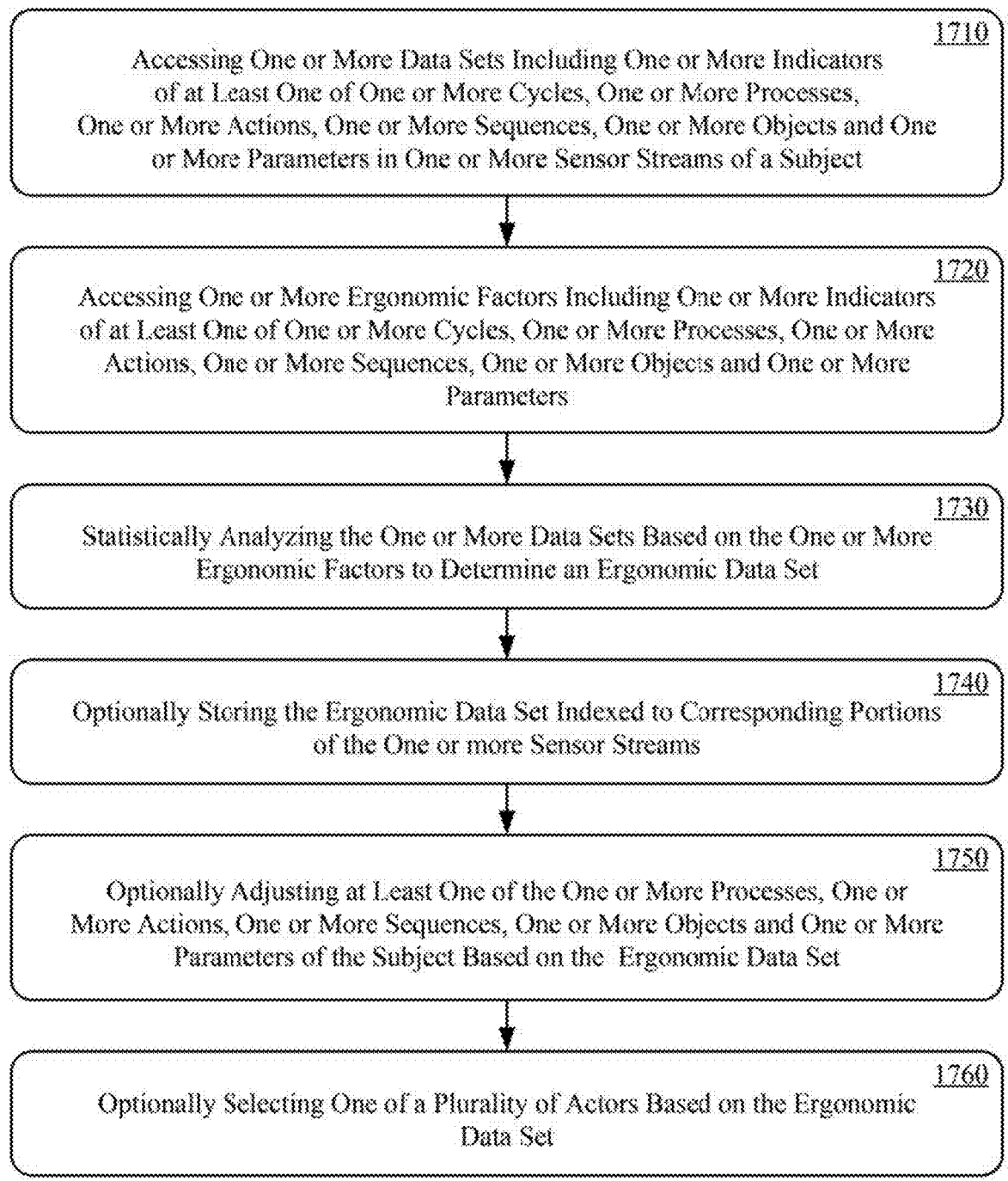
FIG. 17 shows a machine learning based ergonomics method, in accordance with aspects of the present technology.

Referring now to FIG. 17, a machine learning based ergonomics method, in accordance with aspects of the present technology, is shown. The method can include accessing one or more data sets including one or more identifiers of at least one of one or more cycles, one or more processes, one or more actions, one or more sequences, one or more objects and one or more parameters in one or more sensor streams of a subject, at 1710. The subject can be an article of manufacture, a health care service, a warehousing, a shipping, a restaurant transaction, a retailing transaction or the like. The one or more sensor streams can be received from one or more stations disposed at various position in a work space of a manufacturing, health care, warehouse, shipping, restaurant, retail or the like facility.

In one implementation, the indicators of the cycles, processes, actions, sequences, objects, and parameters of the one or more data sets can include spatio-temporal information such as one or more locations of one or more portions of one or more actors, one or more moments of work (e.g., weight, torque, distance), one or more work zones and or the like. For example, the indicators of the cycles, processes, actions, sequences, objects and or parameters can include one or more locations of one or more portions of a worker captured in the one or more sensor streams. The sensor streams for example include video from one or more cameras disposed at one or more stations. Since, the camera may not always be placed orthogonal to a worker, the data from the camera can be distorted based on the viewpoint of the camera. Using the coordinates of the camera and image projection techniques, the position of the workers hands, legs, head, back and or the like can be established. The data sets can therefore include spatial data, collected at a second or sub-second rate, over one or more manufacturing cycles, for example. The position information can be captured in time and two-dimensions (such as x and y coordinates), or three-dimensions (such as combinations of x, y, z, roll, pitch, and yaw). In one implementation, a point cloud map, a heat map or the like of the places in the work space that the worker reaches out to can be constructed from the spatio-temporal data captured in the data set. In another implementation, the date set can include motion data, for example from a workers' hands starting position (e.g., x, y, z) to ending position (e.g., x1, y1, z1).

The data sets can be based on one or more cycles, one or more actors, one or more stations, and or the like and any combinations thereof. For example, the one or more data sets can include one or more data sets for a first actor and one or more data set for a second actor. In another example, the one or more data sets can include data sets for one or more cycles across each of a plurality of stations of an assembly line. In another example, the one or more data set can include data sets for a specific actor over a specified period of time.

In one implementation, the one or more engines 170 can be configured to retrieve the one or more identifiers of at least one of one or more cycles, one or more processes, one or more actions, one or more sequences, one or more objects and one or more parameters indexed to corresponding portions of the one or more sensor streams from one or more data structures stored in one or more data storage units 175. In another implementation, the one or more engine 170 can generate in real time the one or more identifiers of at least one of one or more cycles, one or more processes, one or more actions, one or more sequences, one or more objects and one or more parameters indexed to corresponding portions of the one or more sensor streams in accordance with the techniques described above with regard to FIG. 6. The position information of one or more portions of one or more actors can be determined from the one or more sensor streams by the one or more engines 170. The one or more engines 170 can be configured to perform a two-part deep learning tracker. A track start detector can perform an initial identification and localization of one or more portions of an actor, such as the hands of a worker. For each frame of a video, for example, the track start detector can utilize a three-dimensional (3D) convolution based neural network to detect the set of hands of a worker, and determine the location of each detected hand. The location can be estimated in the form of a bounding box (e.g., image axis aligned rectangle) of the detected hand object. A track continuation and end detector can determine if a detected track is continuing in the next frame of the video or if the track has ended. The track continuation and end detector can utilize a light weight, relatively shallow, fast, lost cost two-dimensional (2D) convolution based neural network. The two-dimensional (2D) convolution based neural network can take a sequence of two images at a time to determine if the detected track is continuing. If a track continuation is detected, a new bounding box of the tracked object (e.g., hand) can be generated. The image in the pair of bounding boxes (e.g., previous and new frame) can be used as the initial image and tracked object location for the next pair of images. The track start detection is a harder problem, and therefore the heavy duty three-dimensional (3D) convolution based neural network is needed. On the other hand, once a track start is detected, continuing to track it is a much easier problem. Detecting the continuation of a track is aided by the last know position of the object and also by the motion or lack thereof. Once a track start is detected, for a hand for example, the track start detector does not need to be run anymore. The track start detector therefore does not need to run again until after a track end condition is detected. In one implementation, the track start detector can employ a spatio-temporal 3D convolution with a kernel size of 3×3×d, and a stride of 1×1×1. After the 3D convolution layers, a spatial 2D convolution with a kernel stride of 3×3 and a stride of 1×1 can be performed on each frame. The spatial 2D convolution can be followed by 1×1 convolutions. After the 1×1 convolutions, a softmax layer predicting a track start or no track start in parallel with the bounding box of the track if a track start condition is detected, are provided in parallel. For the track continuation and end detector it is expected that the initial image contains at least one instance of the tracked object along with its bounding box. The initial image can be cropped to a padded version of this bounding how and resized to a fixed size to yield the first input image for the shallow neural network. The same bounding box can also be projected to the second image and a more generous padded version of it can be cropped and resized to the same fixed size. The resulting image can go into eh shallow neural network as the second input image. The images, cropped and resized, can go through different copies, with different weights but the same architecture, of the same shallow neural network. The outputs of these different copies of the neural network can be concatenated and the concatenated vector can be passed through two fully connected layers. The decision of track continued or track ended, as well as the track bounding box, if track continued, can be learned via regression loss functions.

At 1720, one or more ergonomic factors including one or more indicators of at least one of one or more cycles, one or more processes, one or more actions, one or more sequences, one or more objects and one or more parameters can be accesses. The indicators of the cycles, processes, actions, sequences, objects, and parameters of the one or more ergonomic factors can include one or more moment of work limits, hazard scores for corresponding work zones, and or the like. In one implementation, the one or more engines 170 can be configured to retrieve the ergonomic factors from one or more data structures stored, on one or more data storage units 175, of from one or more additional data sources such as an Occupational Safety and Health Administration (OSHA) database.

Figure 18:
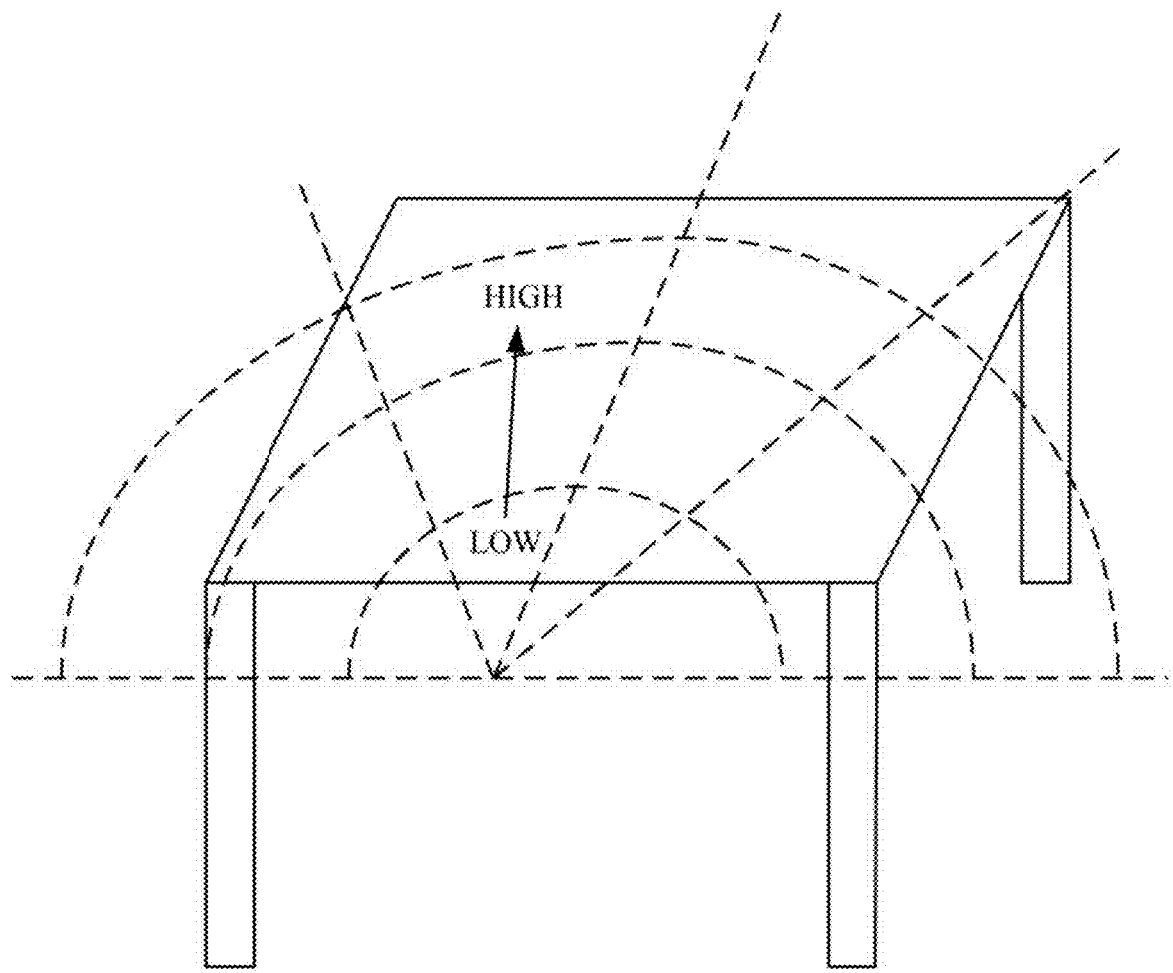
FIG. 18 shows m exemplary work space and hazard zone, in accordance with aspects of the present technology.

In one implementation, a workspace can be divided into a plurality of zones based distances and angle from a fixed reference position of an actor. Hazard scores can be assigned to the plurality of zones, where for example zones near the actor can receive a low hazard score and zones far away or at art unnatural angle of reach can receive a high hazard score, as illustrated in FIG. 18.

At 1730, the one or more data sets can be statistically analyzed based on the one or more ergonomic factors to determine an ergonomic data set. In one implementation, the one or more engines 170 can be configured to analyze the one or more data sets based on the one or more ergonomic factors to generate reach over time studies (e.g., distance), motion over time studies (e.g., distance and frequency), repetitive motion studies (e.g., distance, frequency and count), torque and load studies (e.g., force, frequency and count), and or the like.

At 1740, the ergonomic data set can optionally be stored in one or more data structures. The stored ergonomic data can be indexed to one or more corresponding portions of the one or more sensor streams. In one implementation, the ergonomic data set can be indexed to one or more corresponding portions of the one or more sensor streams by corresponding time stamps. In one implementation, the one or more engines 170 can store the ergonomics data in one or more data structures on one or more data storage units 175. In one implementation, the ergonomics data and the corresponding portions of the one or more sensor streams indexed by the ergonomics data can be blockchained to protect the integrity of the data therein. The blockchaining can be applied across the cycles, sensor streams, stations, supply chain and or the like.

In one implementation, the ergonomic data set and corresponding portions of the one or more sensor streams indexed by the ergonomic data can be stored for a record of the work performed, compliance with ergonomic regulations, and or the like, along with the sensor stream data to back it up.

At 1750, at least one or one or more processes, one or more actions, one or more sequences, one or more objects and one or more parameters of the subject can be adjusted based on the ergonomic data set. In one implementation, one or more processes, actions, sequences, object, parameters and or the like of the subject can be adjusted in addition to storing the ergonomics data set, or alternatively to storing the ergonomics data set. In one implementation, the at least one or one or more processes, one or more actions, one or more sequences, one or more objects and one or more parameters of the subject can be adjusted based on the ergonomic data set to achieve improved placement of tools in the work space, promote working style best practices, and or the like.

At 1760, one of a plurality of actors can be selected based on the ergonomic data set. In one implementation, the actor can be selected based on the ergonomic data set in addition to storing the ergonomics data set or adjusting the at least one or one or more processes, one or more actions, one or more sequences, one or more objects and one or more parameters of the subject. Similarly, the actor can be selected based on the ergonomic data set alternatively to storing the ergonomics data set or adjusting at least one or one or more processes, one or more actions, one or more sequences, one or more objects and one or more parameters of the subject.

Figure 19:
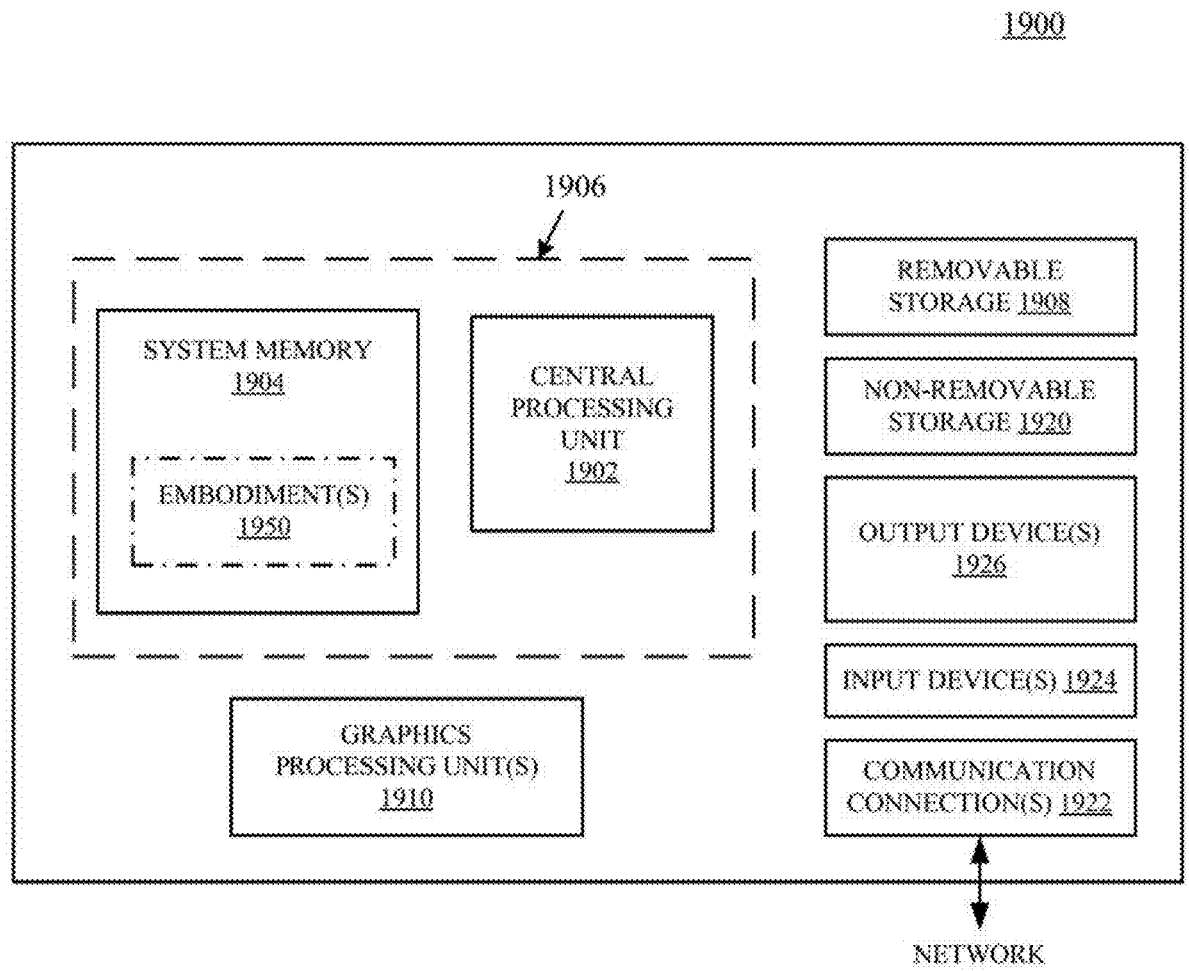
FIG. 19 shows an exemplary computing device, in accordance with aspects of the present technology.

Referring now to FIG. 19, a block diagram of an exemplary computing device upon, which various aspects of the present technology can be implemented. In various embodiments, the computer system 1900 may include a cloud-based computer system, a local computer system, or a hybrid computer system that includes both local and remote devices. In a basic configuration, the system 1900 includes at least one processing unit 1902 and memory 1904. This basic configuration is illustrated in FIG. 19 by dashed line 1906. The system 1900 may also have additional features and/or functionality. For example, the system 1900 may include one or more Graphics Processing Units (GPUs) 1910. Additionally, the system 1900 may also include additional storage (e.g., removable and/or non-removable) including, but not limited to, magnetic or optical disks or tape. Such additional storage is illustrated in FIG. 19 by removable storage 1908 and non-removable storage 1920.

The system 1900 may also contain communications connection(s) 1922 that allow the device to communicate with other devices, e.g., in a networked environment using logical connections to one or more remote computers. Furthermore, the system 1900 may also include input device(s) 1924 such as, but not limited to, a voice input device, touch input device, keyboard, mouse, pen, touch input display device, etc. In addition, the system 1900 may also include output device(s) 1926 such as, but not limited to, a display device, speakers, printer, etc.

In the example pf FIG. 19, the memory 1904 includes computer-readable instructions, data structures, program modules, and the like associated with one or more various embodiments 1950 in accordance with the present disclosure. However, the embodiment(s) 1950 may instead reside in any one of the computer storage media used by the system 1900, or may be distributed over some combination of the computer storage media, or may be distributed over some combination of networked computers, but is not limited to such.

It is noted that the computing system 1900 may not include all of the elements illustrated by FIG. 19. Moreover, the computing system 1900 can be implemented to include one or more elements not illustrated by FIG. 19. It is pointed out that the computing system 1900 can be utilized or implemented in any manner similar to that described and/or shown by the present disclosure, but is not limited to such.

The foregoing descriptions of specific embodiments of the present technology have been preserved for purposes of illustration and description. They are not intended to be exhaustive or to limit the invention to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A machine learning based ergonomics method comprising:
   determining sensed activity information associated with a first actor and an activity space, wherein the sensed activity information includes at least one of one or more cycles, one or more processes, one or more actions, one or more sequences, one or more objects, and one or more parameters of a manufacturing operation and spatio-temporal data of the first actor, the spatio-temporal data comprising a location of the first actor and moments of work of the first actor, the moments of work comprising one or more of a weight, a torque, or a distance, the determining the sensed activity information comprising:
      performing, with a frame feature extractor, a two-dimensional convolution operation on a video frame sensor stream to generate a two-dimensional array of feature vectors;
      determining, with a region of interest detector, a dynamic region of interest in the video frame sensor stream, wherein the region of interest detector and the frame feature extractor share layers of a convolution neural network; and
      processing an area of each video frame of the video frame sensor stream within the dynamic region of interest while discarding areas of the respective video frames outside the dynamic region of interest to determine the sensed activity information;
   analyzing, by artificial intelligence, the determined sensed activity information for the first actor with respect to one or more ergonomic factors including work limit, work zone and hazard score; and
   forwarding feedback based on the analyzing the determined activity information with respect to the one or more ergonomic factors, wherein:
      the sensed activity information is received from sensors monitoring the activity space in real time, the sensors comprising a video sensor that produces the video frame sensor stream;

the determined activity information is analyzed in real time;
the feedback is forwarded in real time; and
the convolution neural network is applied to a plurality of sliding windows to determine the feedback with no computations repeated.

2. The method of claim 1, wherein the feedback includes identification of ergonomically problematic activities.

3. The method of claim 2, wherein the analyzing comprises:
comparing information associated with activity of the first actor within the activity space with identified representative actions; and
identifying a deviation between the activity of the first actor and a representative standard.

4. The method of claim 1, further comprising:
determining sensed activity information associated with a second actor and the activity space, wherein the sensed activity information includes at least one of one or more cycles, one or more processes, one or more actions, one or more sequences, one or more objects, and one or more parameters of a manufacturing operation and spatio-temporal data of the second actor;
analyzing, by the artificial intelligence, the determined sensed activity information for the first actor and the second actor with respect to the one or more ergonomic factors including work limit, work zone and hazard score; and
forwarding feedback based on the analyzing the determined activity information with respect to the one or more ergonomic factors, wherein the feedback includes an identification of a selection between the first actor and the second actor.

5. The method of claim 4, wherein the analyzing comprises:
determining if a deviation from a representative standard associated with a respective one of the first and second actors is within an acceptable threshold; and
identifying a respective one of a plurality of other actors as a potential acceptable candidate to be a replacement actor when the deviation associated with the respective one of the first and second actors is within an acceptable threshold.

6. One or more non-transitory computing device-readable storage mediums storing instructions executable by one or more computing devices to perform a machine learning based ergonomics method comprising:
determining one or more data sets including one or more indicators of at least one of one or more cycles, one or more processes, one or more actions, one or more sequences, one or more objects and one or more parameters of a manufacturing operation and spatio-temporal data of an actor, wherein the determining the one or more data sets comprises:
receiving a video frame sensor stream from a video sensor monitoring the manufacturing operation;
generating a two-dimensional array of feature vectors by performing a two-dimensional convolution operation on the video frame sensor stream with a frame extractor;
determining a dynamic region of interest (RoI) in the video frame sensor stream with an RoI detector, wherein a convolution neural network comprises convolution layers shared by the frame extractor and the RoI detector, wherein the dynamic RoI encloses an area of a video frame of the video frame sensor stream in which a specific action is occurring;
extracting a fixed-sized feature vector from the area within the dynamic RoI; and
analyzing actions within the fixed-sized feature vector of the video frame sensor stream while discarding areas of the video frame of the video frame sensor stream outside the fixed-sized feature vector to determine the one or more data sets;
accessing one or more ergonomic factors including a work limit, a work zone and a hazard score;
statistically analyzing by artificial intelligence in real time the one or more data sets based on the one or more ergonomic factors to determine an ergonomic data set;
adjusting at least one of the one or more processes, one or more actions, one or more sequences, one or more objects and one or more parameters of the manufacturing operation in real time based on the ergonomic data set; and
forwarding feedback in real time based on the ergonomic data set, wherein:
the feedback is determined by applying the convolution neural network to a plurality of sliding windows such that no computations are repeated.

7. The one or more non-transitory computing device-readable storage mediums storing instructions executable by one or more computing devices to perform the machine learning based ergonomics method according to claim 6, further comprising:
storing the ergonomic data set indexed to corresponding portions of one or more sensor streams, the one or more sensor streams comprising the video stream; and
storing the corresponding portions of the one or more sensor streams.

8. The one or more non-transitory computing device-readable storage mediums storing instructions executable by one or more computing devices to perform the machine learning based ergonomics method according to claim 7, wherein the ergonomic data set and the corresponding portions of the one or more sensor streams are blockchained.

9. The one or more non-transitory computing device-readable storage mediums storing instructions executable by one or more computing devices to perform the machine learning based ergonomics method according to claim 6, further comprising:
selecting one of a plurality of actors based on the ergonomic data set.

10. The one or more non-transitory computing device-readable storage mediums storing instructions executable by one or more computing devices to perform the machine learning based ergonomics method according to claim 6, wherein the one or more indicators of at least one of the one or more cycles, one or more processes, one or more actions, one or more sequences, one or more objects and one or more parameters in the one or more data sets include one or more locations of one or more portions of the actor in a workspace.

11. The one or more non-transitory computing device-readable storage mediums storing instructions executable by one or more computing devices to perform the machine learning based ergonomics method according to claim 10, wherein:
the hazard scores of the one or more ergonomic factors include hazard scores for a plurality of zones of the workspace, wherein at least two zones of the workspace have different hazard scores.

12. A system comprising:
one or more data storage units;
a video sensor configured to produce a video frame sensor stream; and
a computing circuit configured to:
   determine one or more data sets in the one or more data storage units including one or more indicators of at least one of one or more cycles, one or more processes, one or more actions, one or more sequences, one or more objects and one or more parameters of a manufacturing operation and spatio-temporal data of a first action, wherein the one or more data sets are determined by:
      performing a two-dimensional convolution operation on the video frame sensor stream to generate a two-dimensional array of feature vectors through a frame feature extractor;
      combining neighboring ones of the feature vectors to determine a dynamic region of interest (RoI) in the video frame sensor stream through an RoI detector, wherein the RoI detector and the frame feature extractor share layers of a convolution neural network; and
      extracting a fixed-sized feature vector from an area of a video frame of the video frame sensor stream within the dynamic RoI and discarding the remaining feature vectors of the video frame, wherein the convolution neural network analyzes actions in the video frame within the dynamic RoI to determine the one or more data sets;
   access one or more ergonomic factors in the one or more data storage units including a work limit, a work zone and a hazard score;
   statistically analyze in real time by one or more processing units the one or more data sets based on the one or more ergonomic factors to determine an ergonomic data set;
   store the ergonomic data set indexed to corresponding portions of the one or more data sets in the one or more data structures on the one or more data storage units; and
   forward feedback in real time based on the ergonomic data set, wherein:
      the convolution neural network determines the feedback in a plurality of sliding windows without repeating computations.

13. The system of claim 12, wherein the computing circuit is further configured to:
blockchain the ergonomic data set and the corresponding portions of the one or more data sets.

14. The system of claim 12, wherein:
the one or more data sets include one or more data sets for a plurality of actors; and
the computing circuit is further configured to:
   select one of a plurality of actors based on the ergonomic data set.

15. The system of claim 12, wherein the ergonomic data set includes one or more of a reach study, a motion study, a repetitive motion study, and a dynamics study.

* * * * *